US008563222B2

(12) United States Patent
Venneman et al.

(10) Patent No.: US 8,563,222 B2
(45) Date of Patent: *Oct. 22, 2013

(54) LITHOGRAPHIC PRINTING PLATE PRECURSOR

(75) Inventors: Jan Venneman, Berchem (BE); Peter Hendrikx, Hamont-Achel (BE); Paul Callant, Edegem (BE); Alexander Williamson, Mortsel (BE)

(73) Assignee: Agfa Graphics NV, Mortsel (BE)

( * ) Notice: Subject to any disclaimer, the term of this patent is extended or adjusted under 35 U.S.C. 154(b) by 634 days.

This patent is subject to a terminal disclaimer.

(21) Appl. No.: 12/601,110

(22) PCT Filed: May 15, 2008

(86) PCT No.: PCT/EP2008/055952
§ 371 (c)(1),
(2), (4) Date: Nov. 20, 2009

(87) PCT Pub. No.: WO2008/145529
PCT Pub. Date: Dec. 4, 2008

(65) Prior Publication Data
US 2010/0159388 A1 Jun. 24, 2010

Related U.S. Application Data

(60) Provisional application No. 60/940,095, filed on May 25, 2007.

(30) Foreign Application Priority Data

May 25, 2007 (EP) .................................... 07108953

(51) Int. Cl.
*G03F 7/031* (2006.01)
*G03F 7/30* (2006.01)

(52) U.S. Cl.
USPC .................... 430/281.1; 430/284.1; 430/302; 430/919; 430/926; 430/288.1

(58) Field of Classification Search
None
See application file for complete search history.

(56) References Cited

U.S. PATENT DOCUMENTS

| 7,527,916 | B2 | 5/2009 | Callant et al. |
| 2005/0255404 | A1 | 11/2005 | Shibuya |
| 2007/0032564 | A1 | 2/2007 | Callant et al. |

FOREIGN PATENT DOCUMENTS

| EP | 1 621 598 A1 | * | 2/2006 |
| EP | 1 621 928 A1 | * | 2/2006 |
| EP | 1 621 598 B1 | | 1/2008 |
| EP | 1 621 928 B1 | | 12/2008 |
| WO | WO 2005/029187 A1 | | 3/2005 |
| WO | WO 2005/111727 A1 | | 11/2005 |
| WO | WO 2006/048443 A2 | | 5/2006 |

OTHER PUBLICATIONS

Yao et al., *J. Org. Chem.*, "Synthesis of two-photon absorbing unsymmetrical branched chromophores through direct tris(bromomethylation) of fluorine," 70:5126-5132 (2005).

* cited by examiner

*Primary Examiner* — Cynthia Hamilton
(74) *Attorney, Agent, or Firm* — Leydig, Voit & Mayer, Ltd.

(57) ABSTRACT

A lithographic printing plate precursor comprising an image-recording layer, said image-recording layer being photopolymerizable upon exposure to light having a wavelength of from 300 to 500 nm and containing a mixture of sensitizers.

15 Claims, No Drawings

LITHOGRAPHIC PRINTING PLATE PRECURSOR

FIELD OF THE INVENTION

The present invention relates to a lithographic printing plate precursor comprising an image-recording layer, said image-recording layer being photopolymerizable upon exposure to light having a wavelength of from 300 to 500 nm and containing a mixture of sensitizers. The invention relates also to a method of making a printing plate.

BACKGROUND OF THE INVENTION

In lithographic printing, a so-called printing master such as a printing plate is mounted on a cylinder of the printing press. The master carries a lithographic image on its surface and a printed copy is obtained by applying ink to said image and then transferring the ink from the master onto a receiver material, which is typically paper. In conventional, so-called 'wet' lithographic printing, ink as well as an aqueous fountain solution (also called dampening liquid) are supplied to the lithographic image which consists of oleophilic (or hydrophobic, i.e. ink-accepting, water-repelling) areas as well as hydrophilic (or oleophobic, i.e. water-accepting, ink-repelling) areas. In so-called 'driographic' printing, the lithographic image consists of ink-accepting and ink-abhesive (ink-repelling) areas and during driographic printing, only ink is supplied to the master.

Printing masters are generally obtained by the so-called computer-to-film (CtF) method wherein various pre-press steps such as typeface selection, scanning, color separation, screening, trapping, layout and imposition are accomplished digitally and each color selection is transferred to graphic arts film using an image-setter. After processing, the film can be used as a mask for the exposure of an imaging material called plate precursor and after plate processing, a printing plate is obtained which can be used as a master. Since about 1995, the so-called 'computer-to-plate' (CtP) method has gained a lot of interest. This method, also called 'direct-to-plate', bypasses the creation of film because the digital document is transferred directly to a plate precursor by means of a so-called plate-setter. A plate precursor for CtP is often called a digital plate.

Digital plates can roughly be divided in three categories: (i) silver plates, which work according to the silver salt diffusion transfer mechanism; (ii) photopolymer plates which contain a is photopolymerizable composition that hardens upon exposure to light and (iii) thermal plates of which the imaging mechanism is triggered by heat or by light-to-heat conversion. Thermal plates are mainly sensitized for infrared lasers emitting at 830 nm or 1064 nm. Typical photopolymer plates are sensitized for visible light, mainly for exposure by an Ar laser (488 nm) or a FD-YAG laser (532 nm). The wide-scale availability of low cost blue or violet laser diodes, originally developed for data storage by means of DVD, has enabled the production of plate-setters operating at shorter wavelength. More specifically, semiconductor lasers emitting from 350 to 450 nm have been realized using an InGaN material. An advantage of violet plate-setters, compared to visible light plate-setters, are the improved safe-light conditions. Laser diodes, emitting violet light with a wavelength around 405 nm (±15 nm) are at present the most important, commercially available, violet laser diodes. Photopolymer plates generally contain a polymerizable monomer, a binder, a photo-initiator and a sensitizing dye. EP-A 985 683, EP-A 1 048 982 and EP-A 1 070 990 disclose a composition comprising a titanocene compound as photo-initiator and specific dyes as sensitizers for the wavelength range from 350 to 450 nm. EP-A 1 035 435 discloses a 1,3-dihydro-1-oxo-2H-indene derivative as sensitizing dye. A wide range of dyes for the wavelength range from 300 to 1200 nm is disclosed in EP-A 1 091 247.

To enable short exposure times with the commercially available blue or violet laser diodes, resulting in a higher throughput (i.e. higher numbers of printing plate precursors that can be exposed in a given time interval) there is a need to increase the sensitivity of the violet sensitive photopolymerizable compositions. EP-A 1 349 006 and WO2005/029187 disclose a photopolymerizable composition using optical brighteners, e.g. distyrylbenzenes, as sensitizers, suitable for exposure with violet laser diodes. In EP-A 1 621 928, a composition is disclosed which is photopolymerizable upon absorption of light in the wavelength range from 300 to 450 nm, the composition comprising a binder, a polymerizable compound, a sensitizer and a photo-initiator, wherein the sensitizer is a fluorene compound that is conjugated via a double or triple bond with an aromatic or heteroaromatic group. Also in EP-A 1 591 242 and 1 688 792, distyryl benzenes are disclosed as efficient sensitizers for the wavelength range of from 300 to 450 nm.

The photopolymerizable compositions described in EP-A 1 349 006, WO2005/029187 and EP-A 1 621 928 are high enough in sensitivity to enable exposure with violet light having an energy density, measured on the surface of the plate, of 100 µJ/cm$^2$ or less.

A problem associated with the above cited sensitizers may be critical crystallization behaviour in the photopolymerizable layer. The formation of crystals may locally decrease the polymerization efficiency, resulting in areas in the imaged parts of the precursor partly or completely removed during development. Since these areas may not sufficiently take up ink during printing, a poor, sometimes unacceptable, printing quality may be obtained. The occurrence of these crystallization defects may become more pronounced when the printing plate precursor is stored before exposure and development, i.e. the storage stability of the precursor is poor.

To avoid the occurrence of crystallization of the sensitizer WO2005/029187 proposes the use of a sensitizer having a solubility in methylethylketone (MEK) of at least 15 g/kg measured at 20° C. Highly preferred sensitizers according to WO2005/029187 are distyrylbenzenes having branched substituents on the benzene rings. However, printing plate precursors comprising these sensitizers may still have a poor storage stability, which may result in printing plates having a poor printing quality due to crystallization defects.

SUMMARY OF THE INVENTION

An object of the present invention is to provide lithographic printing plate precursors comprising an image-recording layer being photopolymerizable upon exposure to light having a wavelength of from 300 nm to 500 nm, characterized in that said precursor has a very good storage stability, a high sensitivity and provides upon exposure and development printing plates with excellent lithographic property.

Another object is to provide a method of making a printing plate wherein a laser emitting light having a wavelength of from 300 nm to 500 nm and preferably having an energy density, measured on the surface of the plate, of 100 µJ/cm$^2$ or less is used and results in printing plates with excellent printing quality.

The first object of the invention is realized by providing a lithographic printing plate precursor comprising an image-recording layer, said image-recording layer comprising a mixture of sensitizers as described herein. Further preferred embodiments are also described.

The second object of the invention is realized by a method of making a printing plate comprising the steps of (i) providing a lithographic printing plate precursor as described herein, (ii) exposing the precursor with a laser emitting light having a wavelength of from 300 nm to 500 nm and preferably having an energy density, measured on the surface of the plate, of 100 μJ/cm² or less, (iii) optionally pre-heating the exposed precursor and (iv) developing the exposed precursor. Further preferred embodiments are also described.

DETAILED DESCRIPTION OF THE INVENTION

Sensitizers

It has been found that lithographic printing plate precursors comprising a mixture of sensitizers wherein said mixture comprises at least two different sensitizers according to formula I,

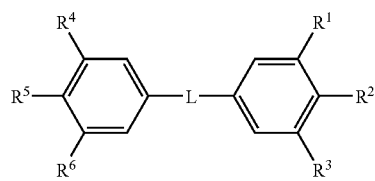

Formula I wherein
$R^1$ to $R^6$ independently represent a hydrogen atom, an optionally substituted alkyl group, an optionally substituted alkoxy group, a cyano group, a halogen atom, a dialkylamino group, an alkylarylamino group or a diarylamino group;
L is an optionally substituted divalent linking group selected from the list consisting of:

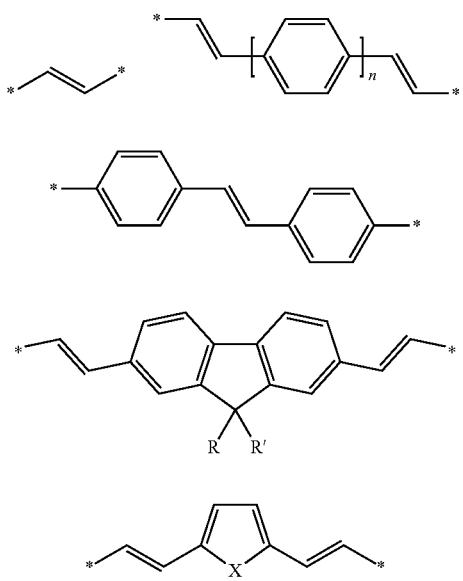

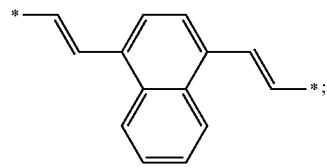

n is an integer from 0 to 2;
X represents S, O or $NR^x$;
* represents the linking positions of the linking group L to the phenyl groups of Formula I;
R, R' and $R^x$ represent an optionally substituted alkyl group;
with the proviso that for at least one sensitizer of said mixture at least one of $R^1$ to $R^6$ contains an asymmetric C-atom and the total amount of sensitizers of which at least one of $R^1$ to $R^6$ contains an asymmetric C-atom is more than 60 percent by weight relative to the total weight of said mixture,
are characterized by an improved storage stability and lithographic properties. It has been found that such a mixture of sensitizers has less tendency to crystallize in the photopolymerizable layer compared to the individual sensitizers and compared to other mixtures of sensitizers.

In a preferred embodiment the mixture of sensitizers is a mixture of sensitizers according to formula II,

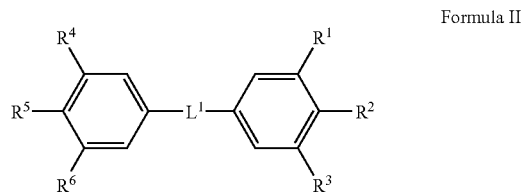

Formula II wherein
$R^1$ to $R^6$ have the same meaning as in Formula I;
$L^1$ is an optionally substituted divalent linking group selected from the list consisting of:

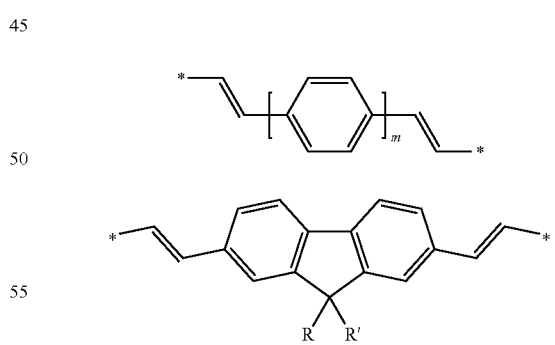

wherein
m is 1 or 2, most preferably m is 1;
R and R' represent an optionally substituted alkyl group;
* represents the linking positions of the linking group $L^1$ to the phenyl groups of Formula II;
with the proviso that for at least one sensitizer of said mixture at least one of $R^1$ to $R^6$ contains an asymmetric C-atom and the total amount of sensitizers of which at least one of $R^1$ to $R^6$ contains an asymmetric C-atom is more than 60 percent by weight, preferably more than 70 percent by weight, relative to the total weight of said mixture.

An asymmetric C-atom is characterized by four different substituents on the C-atom. A sensitizer comprising one asymmetric C-atom is characterized by two stereoisomers also referred to as enantiomers. In the present application, a sensitizer comprising one or more asymmetric C-atoms and therefore characterized by two or more stereoisomers is referred to as one sensitizer. A mixture of stereoisomers of a single sensitizer having one or more asymmetric carbon atom is not a mixture of sensitizers according to the present invention. Different sensitizers referred to in the description and the claims means sensitizers each having a different chemical formula. For example, different sensitizers according to Formula I or II are each, preferably, characterized by at least one different substituent selected from $R^1$ to $R^6$.

Sensitizers according to Formula I or II wherein $R^1=R^4$, $R^2=R^5$ and $R^3=R^6$ are referred to as symmetric sensitizers while those according to Formula I or II wherein $R^1 \neq R^4$ or $R^2 \neq R^5$ or $R^3 \neq R^6$ are referred to as asymmetric sensitizers.

The mixture of the present invention comprises preferably at least one asymmetric sensitizer according to Formula I or II. The total amount of asymmetric sensitizers in the mixture is at least 25, more preferably at least 35, most preferably at least 45 percent by weight relative to the total amount of sensitizers in the mixture.

The alkyl group referred to, also the alkyl group present in the alkoxy groups, means all variants possible for each number of carbon atoms in the alkyl group, i.e. for three carbon atoms: n-propyl and i-propyl; for four carbon atoms: n-butyl, i-butyl, sec-butyl and t-butyl; etc.

The alkyl and alkoxy groups referred to may be substituted for example with a halogen, an ester group, an ether group, a thioether group or a hydroxyl group.

Preferably, $R^1$ to $R^6$ in Formula I or II are alkoxy group, more preferably $R^1$, $R^3$, $R^4$ and $R^6$ are methoxy groups and $R^2$ and $R^5$ are alkoxy groups having 2 to 15 C-atoms, more preferably having 3 to 12 C-atoms, most preferably having 4 to 10 C-atoms.

Most preferably, the mixture of sensitizers according to Formula I or II comprises at least one sensitizer wherein $R^5$ or $R^2$ represents branched alkoxy groups having 3 to 15 C-atoms, more preferably having 4 to 10 C-atoms. Particularly preferred, $R^5$ or $R^2$ are branched alkoxy groups comprising an asymmetric C-atom, e.g. 2-butoxy and 1-(2-ethyl)hexoxy.

The mixture of sensitizers according to Formula I or II comprises at least one sensitizer of which at least one of $R^1$ to $R^6$ comprises an asymmetric C-atom, more preferably said mixture comprises at least two sensitizers of which at least one of $R^1$ to $R^6$ comprises an asymmetric C-atom.

Preferably the mixture of sensitizers according to Formula I or II comprises less than 25 percent by weight, more preferably less than 10 percent by weight, most preferably no sensitizers according to Formula I or II of which the solubility is less than 7.5 percent by weight in 1-methoxy-2-propanol at 80° C. These low soluble sensitizers according to Formula I or II are often characterized by highly symmetric substituents, e.g. $R^2=R^5=$methoxy, 2-propoxy, 3-pentoxy, cyclopentyloxy or cyclohexyloxy.

The mixture of sensitizers comprises at least two, more preferably at least three sensitizers according to Formula I or II. In view of a preferred preparation of the mixture of sensitizers, the mixture preferably comprises 3, 6, 10 or 15, most preferably 3 or 6 different sensitizers.

The mixture of sensitizers according to the present invention may comprise two or more sensitizers according to Formula I or II having the same linking group L or $L^1$ or may comprise two or more sensitizers having a different linking group L or $L^1$.

A solution of a mixture of sensitizers according to Formula I and II can be prepared by adding the individual sensitizers of the mixture to the solution. For this type of mixtures, the individual sensitizers have to be made separately, as described in the examples.

Preferably however, the mixture of sensitizers according to Formula II are prepared in situ by reacting at least two different aldehydes according to Formula III and IV,

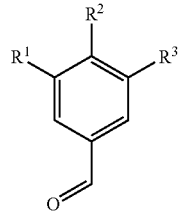

Formula III

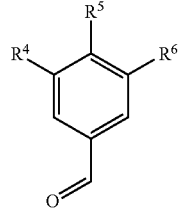

Formula IV with a bis-phosphonate according to Formula V,

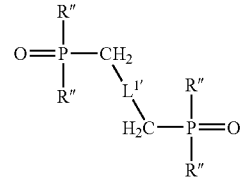

Formula V wherein
$R^1$ to $R^6$ have the same meaning as in Formula I;
R″ represents an alkoxy group or a phenyl group;
$L^{1'}$ represents an optionally substituted divalent linking group selected from the list consisting of:

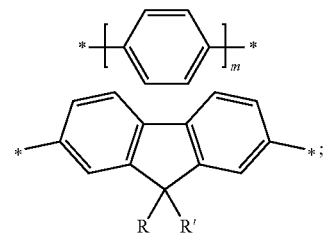

wherein
m is 1 or 2, most preferably wherein m is 1;
* represents the linking positions of the linking group $L^{1'}$;
R and R′ represent an optionally substituted alkyl group.

When two different aldehydes according to Formula III and IV are used, a mixture of three different sensitizers according to Formula II is obtained: two symmetric and one asymmetric sensitizer, as shown in scheme I.

Scheme I

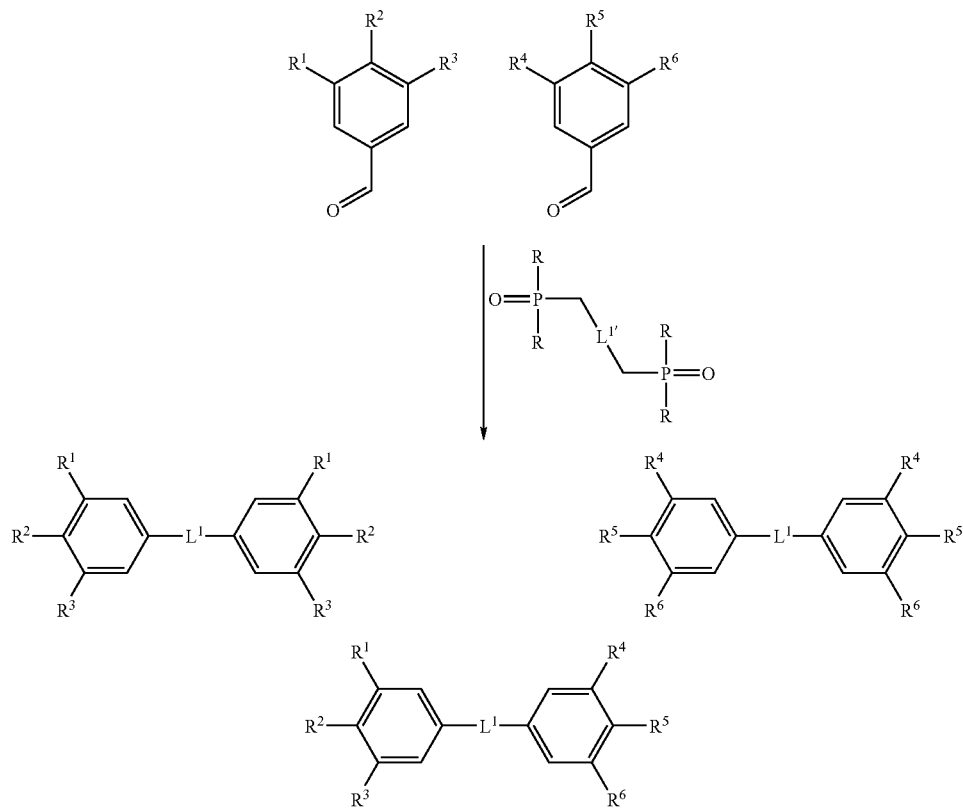

When three different aldehydes are used, a mixture of six different sensitizers according to Formula II is obtained: three symmetric sensitizers and three asymmetric sensitizers. When four different aldehydes are used, a mixture of ten different sensitizers according to Formula II is obtained: four symmetric and six asymmetric sensitizers. Etc.

By varying the relative amount of the different aldehydes, the ratio of the different sensitizers in the mixture can be adjusted.

Preferably, the mixture of sensitizers according to the present invention comprises sensitizers according to Formula I or II, whose absorption spectra are approximately identical, i.e. the absorption maxima of the different sensitizers making up the mixture differ not more than 25 nm, more preferably not more than 10 nm, most preferably not more than 5 nm.

The total amount of sensitizers in the photopolymerizable layer is preferably between 1 and 10 percent by weight, more preferably between 2.5 and 7.5 percent by weight relative to the total amount of non-volatile ingredients.

Photo-Initiator

The photopolymerizable layer comprises one or more photo-initiator(s), capable of initiating a polymerization reaction upon exposure with actinic light, preferably upon exposure with light having a wavelength of from 300 nm to 500 nm, most preferably upon exposure with light having a wavelength of from 350 nm to 450 nm, when used in combination with the mixture of sensitizers according to the present invention.

Known photo-initiators that may be used are: aromatic ketones, aromatic onium salts, organic peroxides, thio compounds, hexaarylbisimidazole compounds, ketooxime ester compounds, borate compounds, azinium compounds, metallocene compounds, active ester compounds and compounds having a carbon-halogen bond. Many specific examples of such compounds are found in EP-A 1 091 247 (paragraph to [0095]), WO2005/111 717 (page 16 to page 31) and EP-A 1 491 536 (paragraph [0046] to paragraph [0080]). Hexaarylbisimidazole compounds, titanocene compounds, trihalomethyl compounds or onium salts are preferably used as photoinitiators, more preferably titanocene and hexarylbisimadazole compounds. Preferred titanocene compounds are for example described in EP-A 1 491 536 (paragraph [66] and [67]).

Particularly preferred photo-initiators are hexaarylbisimidazole (HABI) compounds. Preparation methods of these compounds are described in DE 1 470 154 and their use in photopolymerizable compositions is described in EP 024 629, EP 107 792, U.S. Pat. No. 4,410,621, EP 215 453 and DE 3 211 312. Preferred derivatives are e.g. 2,4,5,2',4',5'-hexaphenylbisimidazole, 2,2'-bis(2-chlorophenyl)-4,5,4',5'-tetraphenylbisimidazole, 2,2'-bis(2-bromophenyl)-4,5,4',5'-tetraphenylbisimidazole, 2,2'-bis(2,4-dichlorophenyl)-4,5,4',5'-tetraphenylbisimidazole, 2,2'-bis(2-chlorophenyl)-4,5,4',5'-tetrakis(3-methoxyphenyl)bisimidazole, 2,2'-bis(2-chlorophenyl)-4,5,4',5'-tetrakis(3,4,5-trimethoxyphenyl)-bisimidazole, 2,5,2',5'-tetrakis(2-chlorophenyl)-4,4'-bis(3,4-dimethoxyphenyl)bisimidazole, 2,2'-bis(2,6-dichlorophenyl)-4,5,4',5'-tetraphenylbisimidazole, 2,2'-bis(2-nitrophenyl)-4,5,4',5'-tetraphenylbisimidazole, 2,2'-di-o-tolyl-4,5,4',5'-tetraphenylbisimidazole, 2,2'-bis(2-ethoxyphenyl)-4,5,4',5'-tetraphenylbisimidazole and 2,2'-bis(2,6-difluorophenyl)-4,5,4',5'-tetraphenylbisimidazole.

A mixture of two or more different photo-initiators may be used in the present invention.

The amount of the photo-initiator typically ranges from 0.01 to 30 percent by weight, preferably from 0.5 to 20 percent by weight, relative to the total weight of the non volatile components of the photo-polymerizable layer.

Co-Initiator

Co-initiators, as described in EP 107 792, may be present in the photopolymerizable layer to further increase the sensitivity. Preferred co-initiators are sulfur-compounds, especially thiols like for example 2-mercaptobenzothiazole, 2-mercaptobenzoxazole or 2-mercapto-benzimidazole. Other preferred co-initiators are polythiols as disclosed in WO2006/048443 and WO2006/048445. These polythiols may be used in combination with the above described thiols, preferably with 2-mercaptobenzthialole.

The amount of co-initiator generally ranges from 0.01 to 10% by weight, preferably from 0.1 to 2% by weight relative to the total weight of the non volatile components of the photopolymerizable composition.

Polymerizable Compounds

The photopolymerizable layer comprises one or more polymerizable monomer(s) or oligomer(s). Preferred monomer(s) or oligomer(s) are ethylenically unsaturated compounds. These ethylenically unsaturated double bond-containing compounds have at least one, preferably from 2 to 6, terminal ethylenically unsaturated bonds.

Preferred monomers include esters of an unsaturated carboxylic acid (e.g. acrylic acid, methacrylic acid, itaconic acid, crotonic acid, isocrotonic acid, and maleic acid) and an aliphatic polyhydric alcohol compound, such as: ethylene glycol diacrylate, triethylene glycol diacrylate, 1,3-butanediol diacrylate, tetramethylene glycol diacrylate, propylene glycol diacrylate, neopentyl glycol diacrylate, trimethylolpropane triacrylate, trimethylolpropane tri(acryloyloxypropyl) ether, trimethylolethane triacrylate, hexanediol diacrylate, 1,4-cyclohexanediol diacrylate, tetraethylene glycol diacrylate, pentaerythritol diacrylate, pentaerythritol triacrylate, pentaerythritol tetraacrylate, dipentaerythritol diacrylate, dipentaerythritol pentaacrylate, dipentaerythritol hexaacrylate, sorbitol triacrylate, sorbitol tetraacrylate, sorbitol pentaacrylate, sorbitol hexaacrylate, tri(acryloyloxyethyl) isocyanurate, tetramethylene glycol dimethacrylate, triethylene glycol dimethacrylate, neopentyl glycol dimethacrylate, trimethylolpropane trimethacrylate, trimethylolethane trimethacrylate, ethylene glycol dimethacrylate, 1,3-butanediol dimethacrylate, hexanediol dimethacrylate, pentaerythritol dimethacrylate, pentaerythritol trimethacrylate, pentaerythritol tetramethacrylate, dipentaerythritol dimethacrylate, dipentaerythritol hexamethacrylate, dipentaerythritol pentamethacrylate, sorbitol trimethacrylate, sorbitol tetramethacrylate, bis[p-(3-methacryloxy-2-hydroxypropoxy)phenyl]dimethylmethane, and bis[p-(methacryloxyethaxy)phenyl]dimethylmethane, ethylene glycol diitaconate, propylene glycol diitaconate, 1,5-butanediol diitaconate, 1,4-butanediol diitaconate, tetramethylene glycol diitaconate, pentaerythritol diitaconate, and sorbitol tetraitaconate, ethylene glycol dicrotonate, tetramethylene glycol dicrotonate, pentaerythritol dicrotonate, sorbitol tetradicrotonate, ethylene glycol diisocrotonate, pentaerythritol diisocrotonate, and sorbitol tetraisocrotonate, ethylene glycol dimaleate, triethylene glycol dimaleate, pentaerythritol dimaleate and sorbitol tetramaleate.

Other preferred monomers include amides of an unsaturated carboxylic acid and an aliphatic polyhydric amine compound, such as: methylene bisacrylamide, methylene bismethacrylamide, 1,6-hexamethylene bisacrylamide, 1,6-hexamethylene bismethacrylamide, diethylenetriamine trisacrylamide, xylylene bisacrylamide and xylylene bismethacrylamide.

Other preferred monomers include urethane compounds containing two or more ethylenically unsaturated bonds. These polymerizable compounds are reaction products of a polyisocyanate compound, containing two or more isocyanate groups, with a multifunctional alcohol of which the hydroxyl groups are partly or completely esterified with (meth)acrylic acid. Particularly preferred compounds are prepared by reacting hydroxyalkyl(meth)acrylates with diisocyanates, as disclosed in DE 28 22 190 and DE 20 64 079.

Other preferred monomers contain primary, secondary and in particular tertiary amino groups, thio or enol groups, as disclosed in EP 1 349 006 (paragraph [0014] to [0024]). An example of a particularly preferred monomer is:

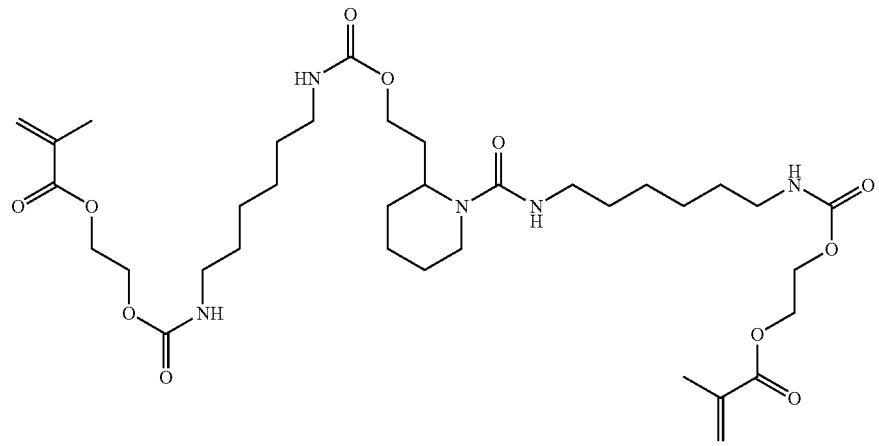 [SMILES: C=C(C)C(=O)OCCOC(=O)NCCCCCCNC(=O)OCCC1CCCCN1C(=O)NCCCCCCNC(=O)OCCOC(=O)C(=C)C]

The total amount of polymerizable compounds typically ranges from 10 to 90 percent by weight, preferably from about 20 to 80 percent by weight, relative to the total weight of the non volatile components of the photopolymerizable layer.

Binder

The binder of the photopolymerizable layer may be selected from a wide series of organic polymers or co-polymers. Also a mixture of two or more different polymers or co-polymers may be used.

The selected binder may be different dependent on the development process of the printing plate precursor, to ensure complete removal of the non-image areas of the photopolymerizable layer during development.

Suitable polymers to be used as binder may include (meth) acrylic resins, polyvinyl acetal resins, polyurethane resins, polyamide resins, epoxy resins, polystyrene resins and polyester resins.

Preferred polymers or co-polymers usable as binder are disclosed in WO2005/111727 (page 17 ln. 21 to page 20 ln. 3) and WO2005/029187 (page 16 ln. 26 to page 18 ln. 11).

In the embodiment wherein an alkaline developer is used in the development process the binder is preferably insoluble in water, but soluble or at least swellable in aqueous-alkaline solutions. Preferred binders contain an acid group such as a carboxyl group, a sulfone group or a phosphate group. Particularly preferred and well known are polymers or co-polymers containing carboxyl groups, in particular polymers or co-polymers containing monomeric units of α,β-unsaturated carboxylic acids and/or monomeric units of α,β-unsaturated dicarboxylic acids. Specific examples are polymers or co-polymers of acrylic acid, methacrylic acid, crotonic acid, vinylacetic acid, maleic acid or itaconic acid. Preferred binders have an acid number, expressed as mg KOH/g polymer, of from 10 to 250, preferably from 20 to 200.

When the development is carried out in a gum solution or on press by applying ink and/or fountain solution, the binder preferably does not substantially contain an acid group. Such binders preferably have an acid number, expressed as mg KOH/g polymer of 20 or less, more preferably of 10 or less. Preferred binders are (meth)acrylic acid ester co-polymers, such as a co-polymer of a (meth)acrylic acid alkyl or aralkyl ester with a (meth)acrylic acid ester containing a —CH$_2$—CH$_2$—O— or —CH$_2$—CH$_2$—NH— unit in R of the ester residue (—COOR) of the (meth)acrylic ester. The alkyl group in the (meth)acrylic acid alkyl ester is preferably an alkyl group having from 1 to 5 carbon atoms, more preferably a methyl group. Preferred examples of the (meth)acrylic acid aralkyl ester include benzyl(meth)acrylate.

In view of improving the developing properties in an aqueous solution, the binder preferably comprises hydrophilic groups, e.g. a hydroxyl group, a carboxylate group, a hydroxyethyl group, an ethyleneoxy group, an aminopropyl group, an ammonium group, an amido group or a carbomethyl group.

Particularly suitable binders when development is carried out in a gum solution or on-press are copolymers of vinylacetate and vinylalcohol comprising vinylalcohol in an amount of 10 to 98 mol %, preferably between 35 and 95 mol %, more preferably between 40 and 75 mol %, particularly preferred between 50 and 65 mol % vinyl-alcohol. The ester-value, measured by the method as defined in DIN 53 401, of the copolymers of vinylacetate and vinylalcohol ranges preferably between 25 and 700 mg KOH/g, more preferably between 50 and 500 mg KOH/g, most preferably between 100 and 300 mg KOH/g. The viscosity of the copolymers of vinylacetate and vinylalcohol are measured on a 4 weight % aqueous solution at 20° C. as defined in DIN 53 015 and the viscosity ranges preferably between 3 and 60 mPa·s, more preferably between 4 and 30 mPa·s, most preferably between 5 and 25 mPa·s. The average molecular weight $M_W$ of the copolymers of vinylacetate and vinylalcohol ranges preferably between 5 000 and 500 000 g/mol, more preferably between 10 000 and 400 000 g/mol, most preferably between 15 000 and 250 000 g/mol.

Other particularly preferred binders for the embodiment wherein development is carried out in a gum solution or on press are copolymers of vinylacetals, vinylacetate and vinylalcohol. These copolymers may be prepared starting from polyvinylacetates: the polyvinylacetate is first partially hydrolyzed to form a copolymer of vinylacetate and vinylalcohol, followed by a partially acetylization of the vinylalcohol by reaction with an aldehyde. The most common aldehydes are formaldehyde and butyraldehyde resulting in vinylformal or vinylbutyral, preferably vinylbutyral. The vinylbutyral monomers are hydrophobic while the vinylalcohol and/or vinylacetate monomers are hydrophilic. The hydrophobicity of the binder may influence the ink acceptance and the run length while the hydrophilicity of the binder may influence the developability, especially when development is carried out on press or in a gum solution. By adjusting the ratio vinylbutyral versus vinylalcohol and vinylacetate, the hydrophobicity-hydrophilicity of the binder may be optimized. A partial esterification of the co-polymer with polycarboxylic acids, e.g. trimellit acid, may introduce carboxylic acid groups into the co-polymer to further optimize the hydrophobicity-hydrophilicity of the binder.

When the development is carried out in a gum solution or on-press by applying ink and/or fountain solution, the photopolymerizable layer may also comprises a polymer as described in the unpublished PCT/EP2006/068619 (filed on 2006, Nov. 17). According to this preferred embodiment the photopolymerizable layer comprises a polymer containing an acid group and a basic nitrogen-containing compound capable of neutralizing said acid group, or said photopolymerizable layer comprises a polymer containing an acid group which is neutralized by a basic nitrogen-containing compound.

The binder may also comprise a crosslinkable functional group in the main chain or a side chain. A crosslinkable group is capable of crosslinking the polymeric binder upon exposure. The crosslinkable functional group may be an ethylenically unsaturated group, an amino group, an epoxy group, a thiol group, a halogen atom or an onium salt. Preferably, the polymeric binder contains an ethylenically unsaturated group. Examples of suitable crosslinkable binders are discloses in EP 1 748 317 (paragraph [0075] to [0084]). The content of the crosslinkable group (content of radical-polymerizable unsaturated double bond determined by iodine titration) in the binder polymer is preferably from 0.1 to 10.0 mmol, more preferably from 1.0 to 7.0 mmol, and most preferably from 2.0 to 5.5 mmol, per g of binder polymer. The crosslinking property of the binder may increase the durability of the image-areas of the printing plate and therefore improve the run length.

The organic polymers used as binders have a typical mean molecular weight $M_W$ between 600 and 200 000, preferably between 1 000 and 100 000.

The amount of binder(s) generally ranges from 10 to 90% by weight, preferably 20 to 80% by weight, relative to the total weight of the non-volatile components of the composition.

The total amount of the polymerizable compounds relative to the total amount of binder is preferably from 4.0 to 0.5, more preferably from 2.0 to 1.0.

Hydrophilic Polymer

A hydrophilic polymer may be added to the photopolymerizable layer to enhance the developability. Suitable examples of the hydrophilic polymer include those having a hydrophilic group such as a hydroxyl group, a carboxyl group, a carboxylate group, a hydroxyethyl group, a polyoxyethyl group, a hydroxypropyl group, a polyoxypropyl group, an amino group, an aminoethyl group, an aminopropyl group, an ammonium group, an amide group, a carboxymethyl group, a sulfonic acid group and a phosphoric acid group. Specific examples thereof include gum arabic, casein, gelatin, starch derivatives, carboxymethylcellulose and sodium salts thereof, cellulose acetate, sodium alignate, cinul acetate-maleic acid co-polymers, styrene-maleic acid co-polymers, polyacrylic acids and salts thereof, poly(meth)acrylic acids and salts thereof, homopolymers and co-polymers of hydroxyethyl(meth)acrylate, homopolymers and co-polymers of hydroxypropyl(meth)acrylate, homopolymers and co-polymers of hydroxybutyl(meth)acrylate, polyethylene glycols, hydroxypropylene polymers, polyvinyl alcohols, hydrolyzed polyvinyl acetates, polyvinyl formal, polyvinyl butyral, polyvinyl pyrrolidone, homopolymers and polymers of (meth) acrylamide. The hydrophilic polymer preferably has a weight average molecular weight of 5 000 or more, more preferably from 10 000 to 300 000. The hydrophilic polymer may be a random polymer, a block polymer or a graft polymer. The content of the hydrophilic polymer in the image-recording layer is preferably 20 percent by weight or less, more preferably 10 percent by weight or less, relative to the entire solid content of the image-recording layer.

Particularly preferred hydrophilic polymers are those disclosed in the unpublished EP-A 06 120 509 wherein the hydrophilic polymer is a polymer having at least 1 mol percent of a monomeric unit capable of interacting with the support and at least 30 mol percent of a hydrophilic monomeric unit. In EP-A 06 120 509 the hydrophilic polymer is used in combination with a non-polymeric adhesion promoting compound, said compound comprising a group capable of interacting with the aluminum surface. The hydrophilic polymer and the adhesion promoting compound may also be incorporated in an intermediate layer, positioned between the support and the image-recording layer.

Contrast Dye

The coating of the lithographic printing plate may further comprise a colorant. The colorant can be a dye or a pigment. After development with a gum solution or with an alkaline developer, at least part of the colorant remains in the hardened coating areas and provides a visible image, enabling an examination of the lithographic image on the developed printing plates. Preferred dyes and/or pigments are disclosed in WO 2005/111727. Highly preferred pigments are predispersed phthalocyanines. Their amount generally ranges from about 1 to 15% by weight, preferably from about 2 to 7% by weight, with respect to the total weight of the non-volatile compounds in the photosensitive composition. Particularly suitable predispersed phthalocyanine pigments are disclosed in DE 199 15 717 and DE 199 33 139. Preference is given to metal-free phthalocyanine pigments.

The photopolymerizable composition may also comprise compounds that undergo discoloration or coloration upon exposure with violet light. Compounds that undergo discoloration or coloration by radicals or acids, generated by the violet exposure, are preferred. Especially for the on-press processing embodiment of this invention, such compounds give rise to a print-out image enabling inspection of the image to be printed. Various dyes may be used for this purpose, e.g. diphenylmethane, triphenylmethane, thiazine, oxazine, xanthene, anthraquinone, iminoquinone, azo and azomethine dyes.

Other Ingredients

The photopolymerizable composition may further comprise other ingredients such as for example surfactants, polymerization inhibitors, plasticizers, inorganic particles, low molecular weight hydrophilic compounds.

Preferred inhibitors for use in the photopolymer coating are disclosed in U.S. Pat. No. 6,410,205, EP 1 288 720 and WO2005/109103. Various surfactants may be added to the photopolymerizable layer. Both polymeric and small molecule surfactants can be used. Nonionic surfactants are preferred. Preferred nonionic surfactants are polymers and oligomers containing one or more polyether segments (such as polyethylene glycol, polypropylene glycol, and copolymer of ethylene glycol and propylene glycol). Examples of preferred nonionic surfactants are block copolymers of propylene glycol and ethylene glycol (also called block copolymer of propylene oxide and ethylene oxide); ethoxylated or propoxylated acrylate oligomers; and polyethoxylated alkylphenols and polyethoxylated fatty alcohols. The nonionic surfactant is preferably added in an amount ranging between 0.1 and 30% by weight of the coating, more preferably between 0.5 and 20%, and most preferably between 1 and 15%.

Overcoat

The coating preferably comprises a top layer, also referred to as overcoat layer, overcoat or protective layer and typically applied onto the image-recording layer, which acts as an oxygen barrier layer.

Preferred binders which can be used in the top layer are disclosed in WO2005/029190 (page 36 line 3 to page 39 line 25), US 2007/0020563 (paragraph [0158]) and EP 1 288 720 (paragraphs [0148] and [0149]). The most preferred binder for the top layer is polyvinylalcohol. The polyvinylalcohol has preferably a hydrolysis degree ranging between 74 mol % and 99 mol %. The weight average molecular weight of the polyvinylalcohol can be determined by measuring the viscosity of a 4% by weight aqueous solution at 20° C., as defined in DIN 53 015. This viscosity number ranges preferably between 3 and 26, more preferably between 3 and 15, most preferably between 3 and 10. Preferably, a mixture of polyvinylalcohols having a different hydrolysis and viscosity number are used.

Modified polyvinylalcohols, e.g. polyvinylalcohols having a carboxyl group and/or a sulphonic acid group may also be used, preferably together with unmodified polyvinylalcohols.

The coating thickness of the top layer is preferably between 0.25 and 1.75 g/m$^2$, more preferably between 0.30 and 1.30 g/m$^2$, most preferably between 0.40 and 1.00 g/m$^2$. In a most preferred embodiment of the present invention, the top layer has a coating thickness between 0.25 and 1.75 g/m$^2$ and comprises a polyvinyl-alcohol having a hydrolysis degree ranging between 74 mol % and 99 mol % and a viscosity number as defined above ranging between 3 and 26.

Besides acting as barrier for oxygen, the overcoat layer must be easily removable during processing and be sufficiently transparent for the actinic radiation, e.g. from 300 to 500 nm.

The overcoat layer may comprise other ingredients such as anionic surfactants, e.g. sodium alkyl sulphate or sodium alkyl sulphonate; amphoteric surfactants, e.g. alkylaminocarboxylate and alkylamino-dicarboxylate; non-ionic surfactants, e.g. polyoxyethylene alkyl phenyl ether; additives, e.g. alkoxylated alkylene diamines, disclosed in EP 1 085 380 (paragraph [0021] and [0022]); glycerine, inorganic particles, pigments, etc.

Intermediate Layer—Adhesion Promoting Compound

The optional intermediate layer may comprise adhesion promoting compounds. These adhesion promoting compounds may however also be incorporated in the photopolymerizable layer. The adhesion promoting compound is preferably a compound capable of interacting with said support, e.g. a compound having an addition polymerizable ethylenically unsaturated bond and a functional group capable of interacting with the support, more preferably a functional group capable of interacting with a grained and anodised aluminum support. Under "interacting" is understood each type of physical and/or chemical reaction or process whereby, between the functional group and the support, a bond is formed which can be a covalent bond, an ionic bond, a complex bond, a coordinate bond or a hydrogen-bridge bond, and which can be formed by an adsorption process, a chemical reaction, an acid-base reaction, a complex-forming reaction or a reaction of a chelating group or a ligand. The adhesion promoting compound may be selected from at least one of the low molecular weight compounds or polymeric compounds as described in EP-A 851 299 from lines 22 on page 3 to line 1 on page 4, EP-A 1 500 498 from paragraph [0023] on page 7 to paragraph [0052] on page 20, EP-A 1 495 866 paragraph [0030] on page 5 to paragraph [0049] on page 11, EP-A 1 091 251 from paragraph [0014] on page 3 to paragraph [0018] on page 20, and EP-A 1 520 694 from paragraph [0023] on page 6 to paragraph [0060] on page 19. Preferred compounds are those compounds which comprise a phosphate or phosphonate group as functional group capable of adsorbing on the aluminum support and which comprise an addition-polymerizable ethylenic double bond reactive group, especially those described in EP-A 851 299 from lines 22 on page 3 to line 1 on page 4 and EP-A 1 500 498 from paragraph [0023] on page 7 to paragraph [0052] on page 20. Also preferred are those compounds comprising tri-alkyl-oxy silane groups, hereinafter also referred to as "trialkoxy silane" groups, wherein the alkyl is preferably methyl or ethyl, or wherein the trialkyloxy silane groups are at least partially hydrolysed to silanol groups, as functional group capable of adsorbing on the support, especially silane coupling agents having an addition-polymerizable ethylenic double bond reactive group as described in EP-A 1 557 262 paragraph [0279] on page 49 and EP-A 1 495 866 paragraph [0030] on page 5 to paragraph [0049] on page 11. The adhesion promoting compound may be present in the photopolymerizable layer in an amount ranging between 1 and 50% by weight, preferably between 3 and 30% by weight, more preferably between 5 and 20% by weight relative to the total amount of the non-volatile components of the composition. The adhesion promoting compound may be present in the intermediate layer in an amount of at least 50% by weight, preferably at least 80% by weight, more preferably at least 90% by weight, most preferably 100% by weight relative to the total amount of the non-volatile components of the composition. The optionally intermediate layer has a coating thickness preferably ranging between 0.001 and 1.5 g/m$^2$, more preferably between 0.003 and 1.0 g/m$^2$, most preferably between 0.005 and 0.7 g/m$^2$.

Support

A particularly preferred lithographic support is an electrochemically grained and anodized aluminum support. The aluminum support has a thickness of about 0.1-0.6 mm. However, this thickness can be changed appropriately depending on the size of the printing plate used and the plate-setters on which the printing plate precursors are exposed. Graining an anodizing of aluminum supports is well known. The acid used for graining can be e.g. nitric acid or sulfuric acid. The acid used for graining preferably comprises hydrogen chloride. Also mixtures of e.g. hydrogen chloride and acetic acid can be used. The relation between electrochemical graining and anodizing parameters such as electrode voltage, nature and concentration of the acid electrolyte or power consumption on the one hand and the obtained lithographic quality in terms of Ra and anodic weight (g/m$^2$ of $Al_2O_3$ formed on the aluminum surface) on the other hand is well known. More details about the relation between various production parameters and Ra or anodic weight can be found in e.g. the article "Management of Change in the Aluminium Printing Industry" by F. R. Mayers, published in the ATB Metallurgie is Journal, volume 42 nr. 1-2 (2002) pag. 69.

Preferred anodic weights are between 0.5 and 10 g/m$^2$ of $Al_2O_3$, more preferably between 1 and 5 g/m$^2$ of $Al_2O_3$.

A preferred aluminum substrate, characterized by an arithmetical mean center-line roughness Ra less then 0.45 μm is described in EP 1 356 926.

The anodized aluminum support may be subject to a so-called post-anodic treatment to improve the hydrophilic properties of its surface. For example, the aluminum support may be silicated by treating its surface with a sodium silicate solution at elevated temperature, e.g. 95° C. Alternatively, a phosphate treatment may be applied which involves treating the aluminum oxide surface with a phosphate solution that may further contain an inorganic fluoride. Further, the aluminum oxide surface may be rinsed with a citric acid or citrate solution. This treatment may be carried out at room temperature or may be carried out at a slightly elevated temperature of about 30 to 50° C. A further interesting treatment involves rinsing the aluminum oxide surface with a bicarbonate solution. Still further, the aluminum oxide surface may be treated with polyvinylphosphonic acid, polyvinylmethylphosphonic acid, phosphoric acid esters of polyvinyl alcohol, polyvinylsulfonic acid, polyvinylbenzenesulfonic acid, sulfuric acid esters of polyvinyl alcohol, and acetals of polyvinyl alcohols formed by reaction with a sulfonated aliphatic aldehyde. Another useful post-anodic treatment may be carried out with a solution of polyacrylic acid or a polymer comprising at least 30 mol % of acrylic acid monomeric units, e.g. GLASCOL E15, a polyacrylic acid, commercially available from ALLIED COLLOIDS. Another treatment is the so-called sealing of the micropores as described in WO-2005/111717.

Optimizing the pore diameter and distribution thereof of the grained and anodized aluminum surface as described may enhance the press life of the printing plate and may improve the resolution of the printing plate. Avoiding large and deep pores may also improve the toning behaviour of the printing plate.

In the unpublished EP-A 06 110 468 (filed on 2006, Feb. 28) a characterizing method of the surface of a grained and anodized aluminum is disclosed. The parameter 'mean pith depth', calculated according to this characterizing method, correlates with the number and depth of the pits present at the aluminum surface. The mean pith depth of the aluminum surface is preferably less then 2.0 μm, more preferably less then 1.8 μm, most preferably less then 1.5 μm. The standard deviation of the 'mean pith depth' is preferably less then 0.70, more preferably less then 0.50, most preferably less then 0.35.

The grained and anodized aluminum support may be a sheet-like material such as a plate or it may be a cylindrical element such as a sleeve which can be slid around a print cylinder of a printing press.

The support can also be a flexible support, which may be provided with a hydrophilic layer, hereinafter called 'base layer'. The flexible support is e.g. paper, plastic film or aluminum. Preferred examples of plastic film are polyethylene terephthalate film, polyethylene naphthalate film, cellulose acetate film, polystyrene film, polycarbonate film, etc. The plastic film support may be opaque or transparent. The base layer is preferably a cross-linked hydrophilic layer obtained from a hydrophilic binder cross-linked with a hardening agent such as formaldehyde, glyoxal, polyisocyanate or a hydrolyzed tetra-alkylorthosilicate. The latter is particularly preferred. The thickness of the hydrophilic base layer may vary in the range of 0.2 to 25 μm and is preferably 1 to 10 μm. More details of preferred embodiments of the base layer can be found in e.g. EP-A 1 025 992.

Exposure

The method of making a printing plate according to the present invention utilizes a laser emitting light having a wavelength of from 300 nm to 500 nm, more preferably of from 350 to 450 nm and preferably having an energy density measured on the surface of the plate of 100 μJ/cm² or less.

Preferably laser diodes, highly preferably commercially available InGaN-based semiconductor laser diodes having a wavelength of 405 nm, are used to expose the lithographic printing plate precursors. The power of the laser diodes may be between 5 and 200 mW, preferably between 20 mW and 150 mW, most preferably between 50 mW and 80 mW. One laser diode may be used to expose the lithographic printing plate precursors, but also multiple laser diodes may be used.

Three major categories of plate-setters, i.e. apparatuses wherein the lithographic printing plates are image-wise exposed with a laser beam, are known and may be used in the present invention: flat bed, internal drum (ITD) and external drum (XTD) type plate-setters.

A particularly preferred plate-setter, an external drum apparatus emitting one or more scanning laser beams having a wavelength between 390 and 420 nm and an energy density, measured on the surface of the precursor, of 100 μJ/cm² or less, and a method of preparing a printing plate using the plate-setter is disclosed in the unpublished EP-A 06 112 161 (filed 2006, Apr. 3). The pixel dwell time of the scanning laser beam is preferably from 0.5 to 10 microseconds.

Also suitable is the apparatus described in US2006/0001849 comprising an imaging head comprising a plurality of laser diodes emitting light of a wavelength between 350 nm and 450 nm. Since each spot on the lithographic printing plate to be exposed receives light, emitted from a plurality of laser diodes, low power laser diodes can be used.

The method disclosed in WO2005/111717 comprising image-wise exposing a photopolymerizable lithographic printing plate precursor with an imaging time per pixel of 1 milliseconds or less using a laser light with an emission wavelength of from 250 nm to 420 nm may also be used in the present invention.

Pre-Heat

The lithographic printing plates are optionally subjected to a pre-heat step. In such a pre-heat step, performed after image-wise exposure and before development, the plate precursor is heated to enhance or to speed-up the polymerization and/or crosslinking reaction. The pre-heat step may improve the printing properties, e.g. rendition of small dots or run length, of the printing plate. There is no particular time limit between exposure and pre-heat but the pre-heat step is usually carried out within a time period after exposure of less than 10 minutes, preferably less than 5 minutes, more preferably less than 1 minutes, most preferably the pre-heat is carried out immediately after the image-wise exposing, i.e. within less than 30 seconds. In this heating step, the precursor is heated at a temperature of preferably 80° C. to 150° C., more preferably of 90 to 140° C., most preferably of 100° C. to 130° C. during preferably 1 seconds to 1 minute, more preferably 5 seconds to 45 seconds, most preferably 10 seconds to 30 seconds. The pre-heating unit is preferably provided with heating elements such as IR-lamps, UV-lamps, heated air, a heated metal or silicone rubber roll, etc.

The pre-heating unit is preferably connected with the development apparatus to enable automatic transport from the pre-heating unit to the development apparatus in a single apparatus. Preferably a cooling section is provided between the pre-heating section and the development section of said single apparatus.

The pre-heating unit, the development unit may also be connected to the plate-setter to enable automatic transport of the exposed precursor to first the pre-heating unit and then the developing unit. Again, a cooling section may be provided between the pre-heating unit and the development unit.

Development

Alkaline Developer

Photopolymerizable printing plate precursors are, according to one embodiment of the present invention, developed in an alkaline aqueous solution. In the development step, the complete overcoat layer and the unexposed part of the photosensitive layer are removed. The removal (wash-off) of the overcoat layer and the development of the photosensitive layer can be done in two separate steps in this order, but can also be done in one step simultaneously. Preferably the overcoat layer is washed-off with water before the development step. The wash-off can be done with cold water, but it is preferred to use hot water to accelerate the process.

The developer solution preferably is an aqueous alkaline solution having a pH from 9 to 14, a pH from 11.5 to 13.5 being particularly preferred. The developer solution can contain a small percentage, preferably less than 5 wt. %, of an organic, water-miscible solvent. To adjust the pH of the solution, an alkali hydroxide is preferably used.

Examples of preferred, additional ingredients of the developer solution comprise alone or in combination alkali phosphates, alkali carbonates, alkali bicarbonates, an organic amine compound, alkali silicates, buffering agents, complexants, defoamers, surface active agents and dyes, as described in e.g. EP-A 1 273 972, EP-A 1 521 123, WO2005/111717 and the EP-As 1 722 274 and 1 722 275, but the suitable ingredients are not limited hereto and further ingredients can be used.

The method of development employed is not particularly limited, and may be conducted by immersing and shaking the plate in a developer, physically removing non-image portions while being dissolved in a developer by means of e.g. a brush, or spraying a developer onto the plate so as to remove non-image portions. The time for development is selected so that the non-image portions are adequately removed, and is optionally selected within a range of 5 seconds to 10 minutes. Development can be carried out at room temperature or at elevated temperatures, for example between 25° C. and 50° C., more preferably between 25° C. and 40° C.

Gum Solution

In another preferred embodiment of this invention the developer used in the method as defined in claim 1 is a gum solution. A preferred composition of the gum solution to be used in the present invention is disclosed in WO2005/111727 (page 5 to 11) and in the unpublished EP-A 05 110 943 (filed on 2005, Nov. 18). Development with the gum solution can be performed at room temperature or at elevated temperatures, e.g. between 25 and 50° C. Development can be carried on until the gum solution is exhausted and has to be replaced by a fresh gum solution or the gum solution is constantly regenerated by adding fresh gum solution as a function of the amount of printing plate precursors developed. The gum solution, used for regeneration, can be of the same or different, preferably higher, concentration. The development step of the method as defined in claim 1 may comprise a prewash step as disclosed in the unpublished EP-A 05 110 915 (filed on 2005, Nov. 18). In this method development comprises washing the precursor in a prewashing station by applying water or an aqueous solution to the coating, thereby removing at least part of the toplayer, followed by development of the precursor in a gumming station by applying a gum solution to the coating of the precursor, thereby removing the non-exposed areas of the photopolymerizable layer from the support and gumming the plate in a single step. The development step of this invention may also comprise two gumming steps as disclosed in the unpublished EP-A 05 110 916 and EP-A 05 110 919 (both filed on 2005, Nov. 19). EP-A 05 110 916 describes a development carried out in a gumming station, said gumming station comprises a first and at least a second gumming unit, wherein the precursor is washed in the first gumming unit by applying a gum solution to the coating, thereby removing at least part of the top layer, and wherein, subsequently, the precursor is developed in the second gumming unit with a gum solution, thereby removing non-exposed areas of the photo-polymerizable layer from the support and gumming the plate in a single step. EP-A 05 110 919 describes a development carried out in a gumming station, comprising a first and at least a second gumming unit, wherein the precursor is consecutively developed in said first and said second gumming unit with a gum solution, thereby removing non-exposed areas of the photopolymerizable layer from the support and gumming the plate in a single step.

On Press Development

In another preferred embodiment of this invention the development is carried out on press by applying ink and/or fountain to the image-wise exposed printing plates. The non-exposed areas of the photo-polymerizable layer are removed by dissolution or dispersion by the ink and/or the aqueous fountain solution while the exposed areas are substantially not removed by applying ink and/or fountain. Also for the on press development embodiment the photopolymerizable composition comprises preferably a polymer as described in the unpublished EP-A 05 110 943 and explained in detail above.

Development may also be performed by combining the embodiments for development as described above, e.g. combining development with a gum solution with development on press by applying ink and/or fountain.

After development the printing plate may be subjected to several well known post-development treatments (e.g. drying, baking, rewashing, etc.).

EXAMPLES

Materials

All materials used in the examples were readily available from standard sources such as Aldrich Chemical Co. (Belgium) and Acros (Belgium) unless otherwise specified.

PVA-1: partially hydrolyzed poly(vinyl alcohol); degree of saponification is 88 mol %; viscosity of a 4 wt % aqueous solution at 20° C. is 4 mPa·s.

PVA-2: fully hydrolyzed poly(vinyl alcohol); degree of saponification is 98 mol %; viscosity of an aqueous solution of 4 wt at 20° C. is 6 mPa·s.

PVA-3: partially hydrolyzed poly(vinyl alcohol); degree of saponification is 88 mol %; viscosity of an aqueous solution of 4 wt % at 20° C. is 8 mPa·s.

Acticide: Acticide LA 1206, a biocide commercially available from THOR.

Lupasol P: 50 wt % solution of a polyethylene imine in water, commercially available from BASF.

Lutensol A8: 90 wt % solution of a surface active agent, commercially available from BASF.

Edaplan: 10 wt % solution of Edaplan LA 411, a modified siloxane-glycol copolymer commercially available from MUNZING CHEMIE GMBH, in Dowanol PM.

Dowanol PM: 1-methoxy-2-propanol, commercially available from DOW CHEMICAL COMPANY.

FST426R: a solution containing 88.2 wt % of a reaction product from 1 mole of 2,2,4-trimethyl-hexamethylene-diisocyanate and 2 moles of hydroxyethylmethacrylate (viscosity 3.30 mm$^2$/s at 25° C.).

Mono Z1620: a solution in MEK containing 30.1 wt % of a reaction product from 1 mole of hexamethylenediisocyanate, 1 mole of 2-hydroxyethylmethacrylate and 0.5 mole of 2-(2-hydroxyethyl-piperidine (viscosity 1.7 mm$^2$ at 25° C.).

MEK: methylethylketone.

Heliogene Blue: Heliogene Blue D 7490 dispersion (9.9 wt %, viscosity 7.0 mm$^2$/s at 25° C.), trade name of BASF AG, as defined in EP 1 072 956.

Hostanox 03: a phenolic antioxidant, commercially available from Clariant.

HABI: 2-(2-chlorophenyl)-4,5-diphenyl bisimidazole, commercially available from SUMITOMO.

MET: 2-mercaptobenzithiazole.

KL7177: methacrylic acid-methylmethacrylate copolymer, commercially available from Clariant.

Example 1

Preparation of the Symmetric Sensitizers SS-01 to SS-06

All symmetric sensitizers SS-01 to SS-06 were prepared as disclosed in WO2005/029187. The preparation of SS-04 is described below in detail. SS-01, SS-02, SS-03, SS-05 and SS-06 were obtained using the same reaction scheme.

Preparation SS-04

SS-04 was prepared according to reaction scheme II and III.

Scheme II

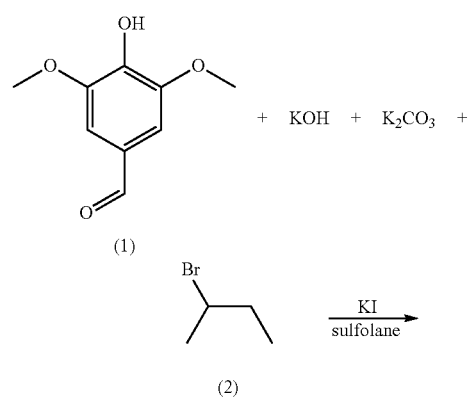

-continued

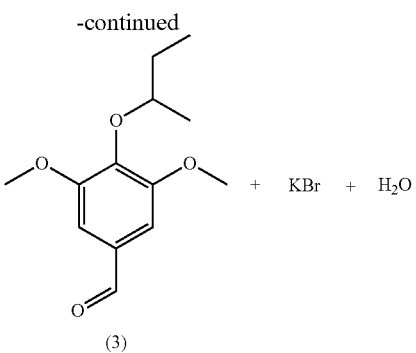

To a mixture of 8.365 kg (45.0 mol) of syringaldehyde (1) and 1.494 kg (9.0 mol) of potassium iodide was added 20.25 l of sulfolane at room temperature. After heating up the mixture to 30° C., 3.12 kg (47.25 mol) of KOH and 2.80 kg (20.25 mol) of $K_2CO_3$ were added. After warming the reaction mixture to 75° C., 12.78 kg (90.0 mol) of 2-bromo butane (2) was added over a period of 30 minutes. Heating at 75° C. was continued for 24 hours, followed by cooling to 25° C. Then, 25 l of water was added and the reaction mixture was extracted with 18 l of methyl t-butyl ether (MTBE). The organic phase was consecutively (i) two times washed with 6.0 l of a 7.5 wt $K_2CO_3$ solution in water, (ii) two times washed with 13.5 l of pure water and finally (iii) two times washed with 4.5 kg of a 20 wt % solution of NaCl in water. The solvent METE was removed by distillation under reduced pressure of 50 mBar at 75° C. 7.845 kg of the intermediate (3) was obtained as yellow oil which was used without purification in the subsequent reaction (see reaction scheme III).

Scheme III

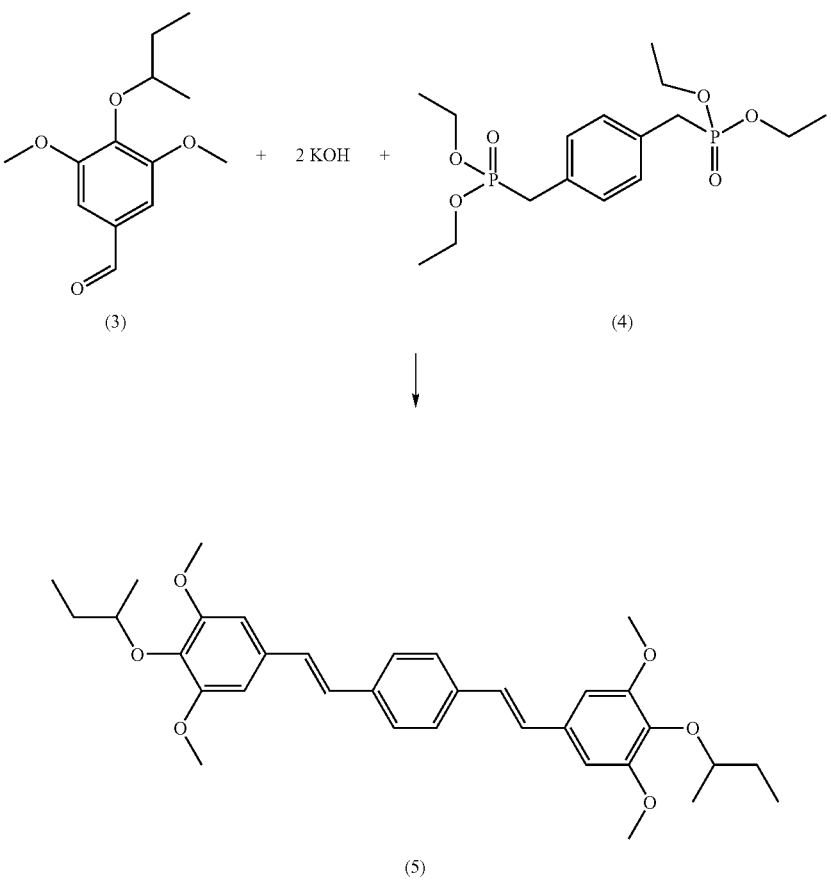

To a mixture of 9.63 kg (25.46 mol) p-xylene-bis-phosphonate (4) and 12.13 kg (50.92 mol) of the crude intermediate (3) in 20 l THF, 4.70 kg (71.3 mol) of KOH was added at room temperature. After heating the stirred reaction mixture at reflux for 3.5 hours, the reaction product was precipitated by adding a mixture of 25.2 kg methanol and 9.9 kg water, followed by further cooling to 20° C. The crystalline product (5) was filtered off, washed with several portions of methanol/water on the filter and dried at 50° C.

The symmetric sensitizers SS-01 to SS-06 are given in Table 1 together with their solubility in methylethylketone (S (MEK)) measured at 20° C.

TABLE 1
| Symmetric Sensitizer | | S (MEK) (wt %) |
|---|---|---|
| SS-01 | 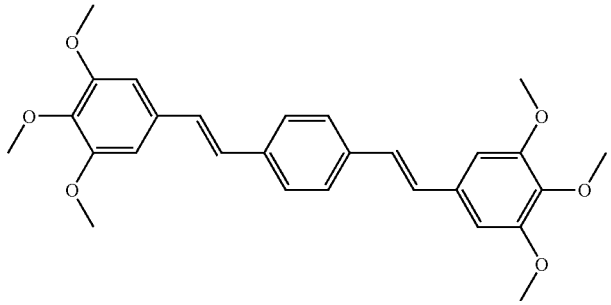 | 0.89 |
| SS-02 | 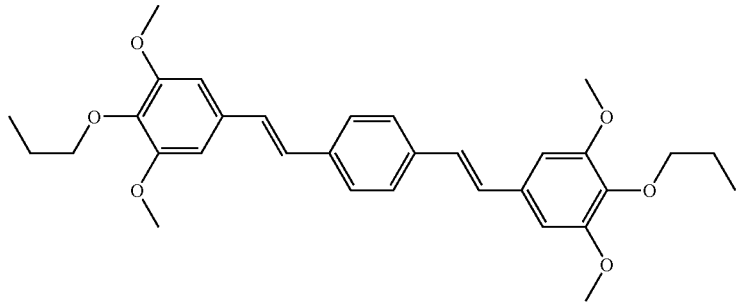 [SMILES: CCCOc1c(OC)cc(/C=C/c2ccc(/C=C/c3cc(OC)c(OCCC)c(OC)c3)cc2)cc1OC] | 4.75 |
| SS-03 | 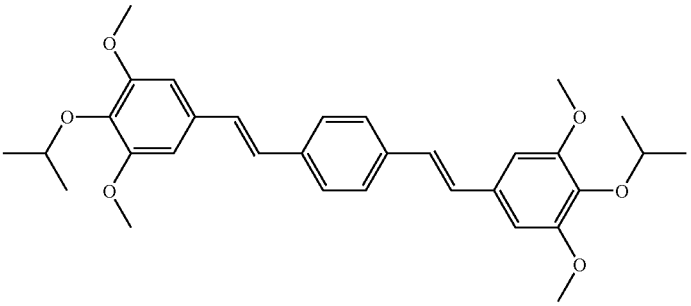 [SMILES: COc1cc(/C=C/c2ccc(/C=C/c3cc(OC)c(OC(C)C)c(OC)c3)cc2)cc(OC)c1OC(C)C] | 0.45 |
| SS-04 | 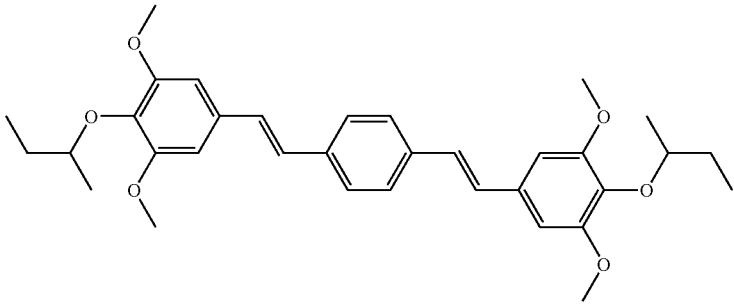 [SMILES: CCC(C)Oc1c(OC)cc(/C=C/c2ccc(/C=C/c3cc(OC)c(OC(C)CC)c(OC)c3)cc2)cc1OC] | 8.71 |
| SS-05 | 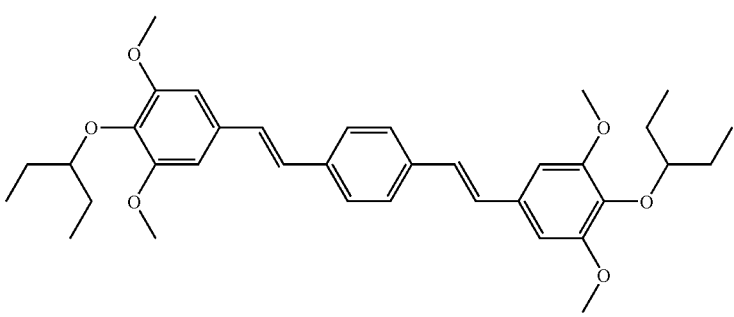 [SMILES: CCC(CC)Oc1c(OC)cc(/C=C/c2ccc(/C=C/c3cc(OC)c(OC(CC)CC)c(OC)c3)cc2)cc1OC] | 9.64 |

TABLE 1-continued
| Symmetric Sensitizer | | S (MEK) (wt %) |
|---|---|---|
| SS-06 | 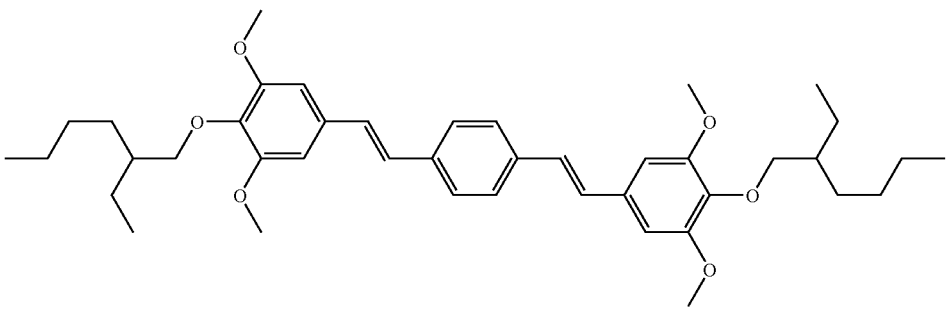 [SMILES: CCCCC(CC)COc1c(OC)cc(/C=C/c2ccc(/C=C/c3cc(OC)c(OCC(CC)CCCC)c(OC)c3)cc2)cc1OC] | 23.21 |
Example 2
Preparation of the Asymmetric Sensitizers AS-01 to AS-05
Synthesis of Asymmetric Sensitizer AS-01
AS-01 was prepared according to reacting scheme IV.
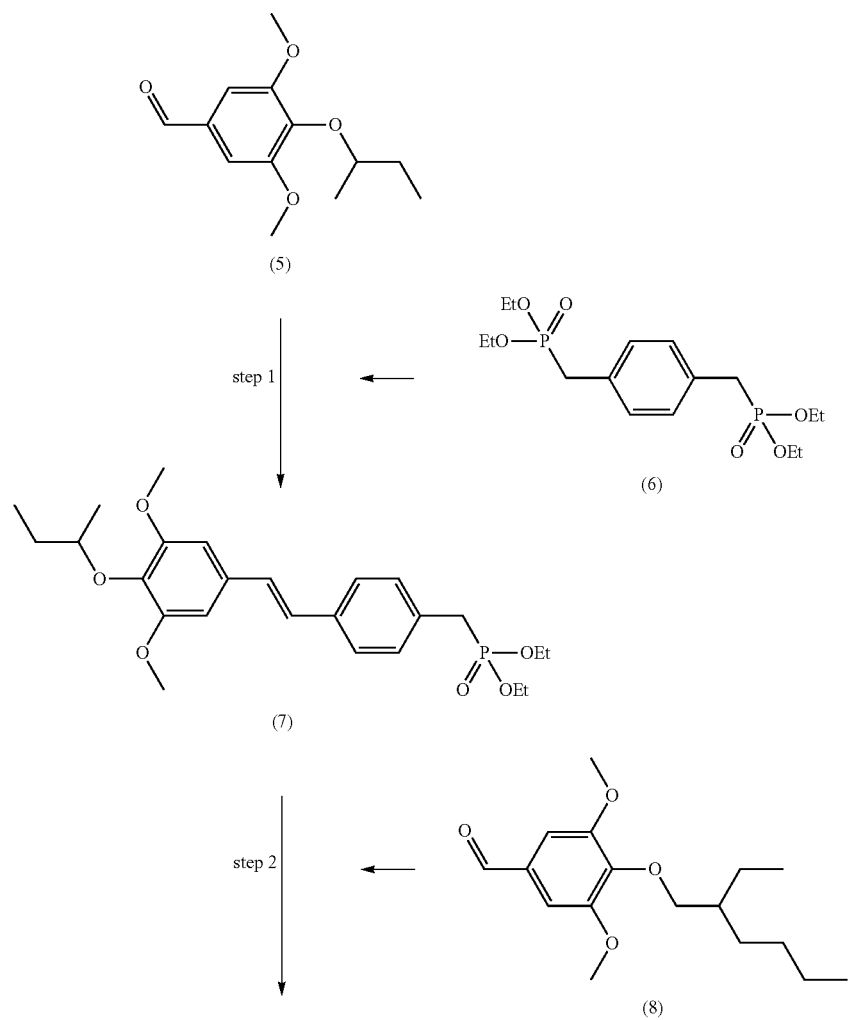

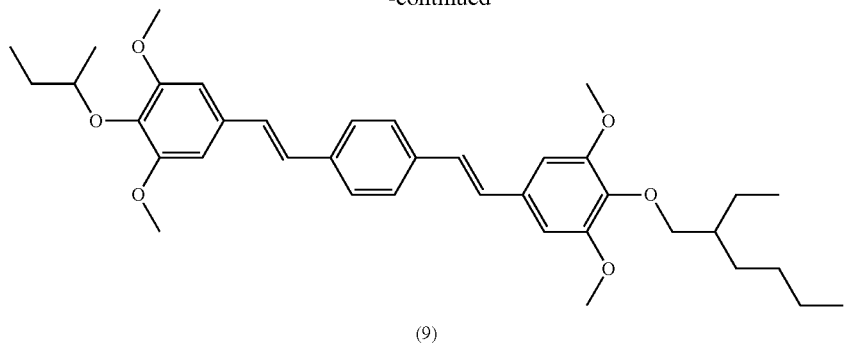

(9)

The intermediates (5) and (8) were prepared as described in WO2005/029187 and Example 1.

Step 1

To a solution of (6) (189 g; 0.5 mol) in ethanol (1.3 l) was added KOH (33 g; 0.55 mol). After warming up to 40° C., a solution of (5) (119 g; 0.5 mol) in ethanol (0.2 l) was added over a 1 hour period, keeping the reaction temperature at 50° C. After 1 hour, an additional portion of KOH (9 g; 0.15 mol) was added and stirring was continued for 2 hours at 55° C. The reaction mixture was concentrated in vacuo with a rotary evaporator, yielding an oil, which was dissolved in ethyl acetate (2.5 l). After washing with aqueous Acetic acid (HOAc) (1 M), water and drying over $MgSO_4$, the solution was concentrated in vacuo with a rotary evaporator, yielding an oil (290 g). This oil was dissolved in methanol (0.6 l) at room temperature.

After cooling to 5° C., a precipitate (56.5 g mainly containing the symmetric SS-04) was filtered off. The solution was concentrated, yielding an oil (140 g) which is purified by preparative column chromatography (silicagel; dichloromethane/ethylacetate 1/1) to obtain (7) (27.1 g; 11.7%) as white crystals.

Step 2

To a solution of (8) (1.65 g; 5.3 mmol) and (7) (2.31 g; 5.0 mmol) in THF (30 ml) at room temperature was added NaH (0.40 g; 7.5 mmol). The reaction mixture was gradually warmed to 50-55° C. and after 30 minutes further heated at 65° C. for another 30 minutes. After adding methanol (50 ml) and concentration of the reaction mixture in vacuo with a rotary evaporator, the crude product (9) was recrystallized (cooling to 10° C.) from methanol/water (100/1). After filtration and washing with methanol the sensitizer AS-01 was obtained (1.70 g; 56%).

The asymmetric sensitizers AS-02, AS-03, AS-04 and AS-05 were obtained using a similar preparation method. The asymmetric sensitizers AS-01 to AS-05 are given in Table 2 together with their absorption maximum (Abs.Max (nm)) and their melting point (° C.).

TABLE 2

| Asymmetric Sensitizer | | Abs · Max (nm) | Melting point (° C.) |
|---|---|---|---|
| AS-01 | | 371 | 81 |
| AS-02 | | 370 | 155 |

TABLE 2-continued

| Asymmetric Sensitizer | | Abs · Max (nm) | Melting point (° C.) |
|---|---|---|---|
| AS-03 | 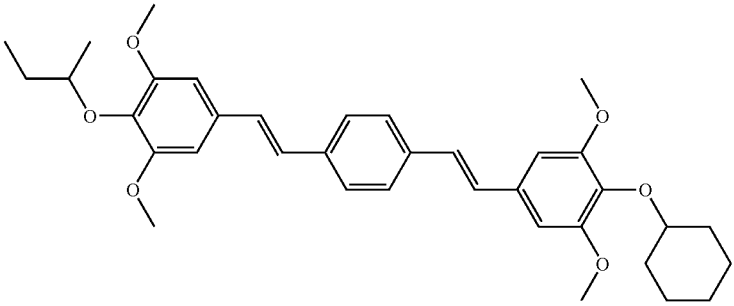 [SMILES: CCC(C)Oc1c(OC)cc(/C=C/c2ccc(/C=C/c3cc(OC)c(OC(CC)CC)c(OC)c3)cc2)cc1OC] | 371 | 165 |
| AS-04 | 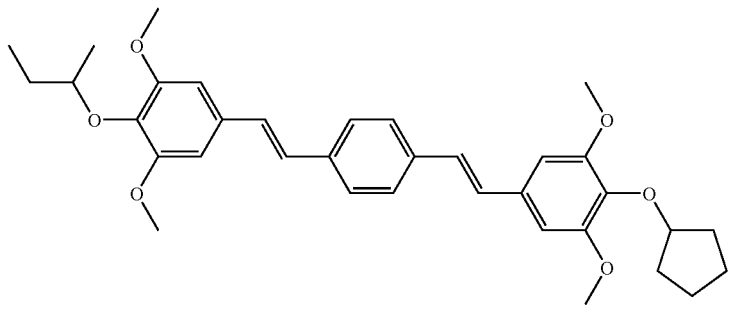 [SMILES: CCC(C)Oc1c(OC)cc(/C=C/c2ccc(/C=C/c3cc(OC)c(OC4CCCC4)c(OC)c3)cc2)cc1OC] | 371 | 153 |
| AS-05 | 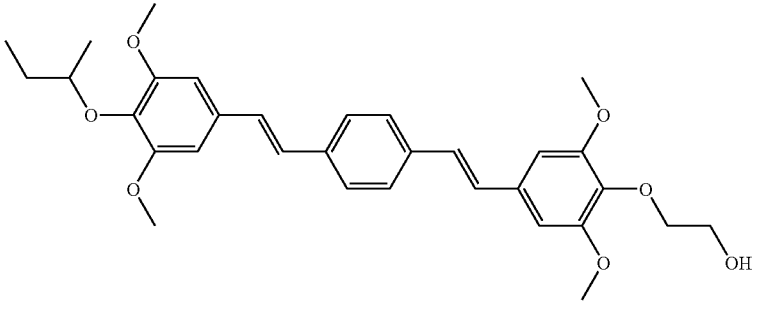 [SMILES: CCC(C)Oc1c(OC)cc(/C=C/c2ccc(/C=C/c3cc(OC)c(OCCO)c(OC)c3)cc2)cc1OC] | 371 | 137 |

Example 3

Preparation of the Mixtures SSMIX-01 to SSMIX-05

The mixtures of sensitizers SSMIX-01 to SSMIX-05 were obtained by adding individual sensitizers in appropriate amounts to 1-methoxy-2-s propanol or the coating solution. The composition of SSMIX-01 to SSMIX-05 is given in Table 3.

TABLE 3

| Mixture | Sensitizer (SS) | | |
|---|---|---|---|
| SSMIX-01 | 33 wt. % SS-04 | 33 wt % SS-05 | 33 wt. % SS-03 |
| SSMIX-02 | 60 wt. % SS-04 | 20 wt % SS-05 | 20 wt. % SS-03 |
| SSMIX-03 | 60 wt. % SS-04 | 40 wt % SS-02 | — |
| SSMIX-04 | 33 wt. % SS-01 | 33 wt % SS-03 | 33 wt. % SS-05 |
| SSMIX-05 | 33 wt. % SS-04 | 33 wt % SS-02 | 33 wt. % SS-06 |

Example 4

Preparation of the Mixtures SSMIX-06 to SSMIX-08

The mixtures of sensitizers SSMIX-06 to SSMIX-08, comprising at least three different sensitizers, were obtained in situ.

Preparation of SSMIX-06

SSMIX-06 has been prepared according to Scheme V.

Scheme V
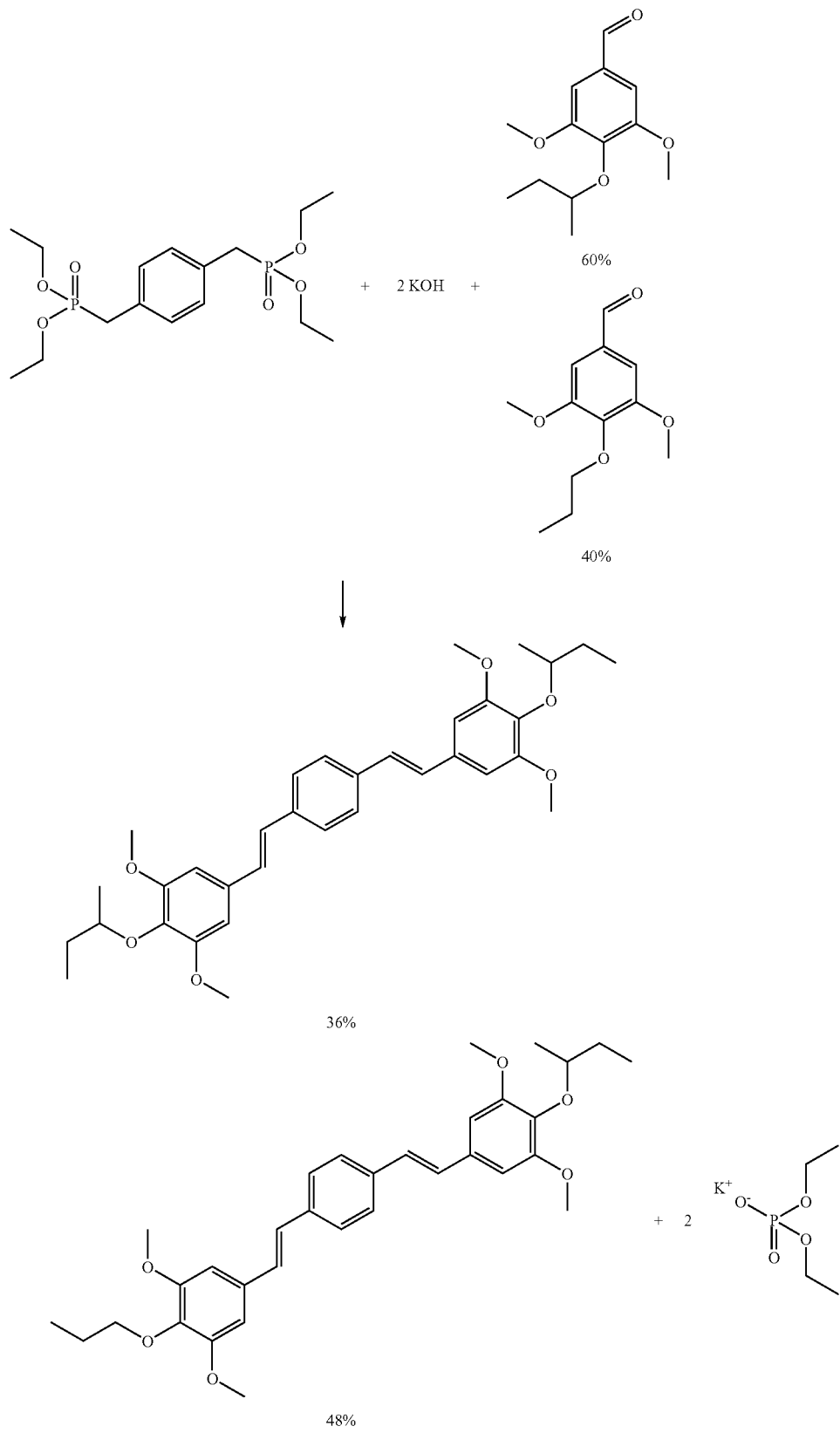

-continued

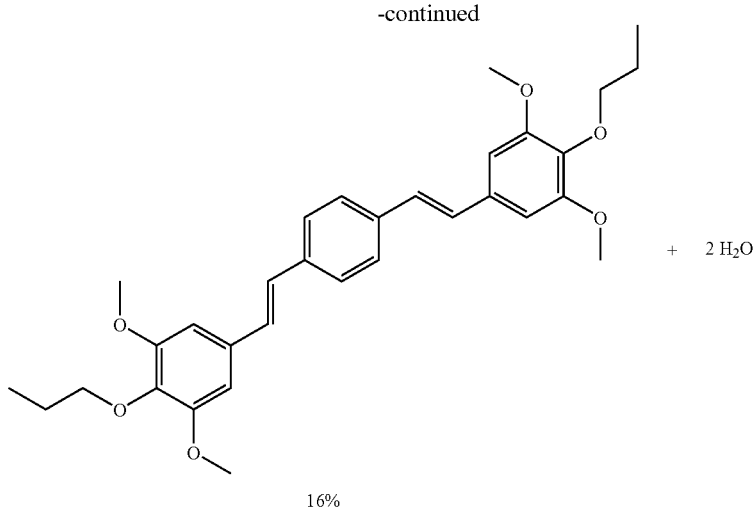

16%

+ 2 H₂O

To a mixture of 6.15 kg (16.25 mol) p-xylene-bis-phosphonate, 3.47 kg (14.95 mol) of the crude intermediate, n-propyl alkylated syringaldehyde, and 5.62 kg (22.43 mol) of the crude intermediate, 1-methyl-propyl alkylated syringaldehyde, in 10.8 kg tetra-hydrofuran (THF), 3.11 kg (47.1 mol) of potassium hydroxide (KOH) was added at room temperature. After heating the stirred reaction mixture at reflux for 3.5 hours, the reaction product was crystallized by adding a mixture of 16.1 kg Methanol (MeOH) and 6.3 kg of water, followed by further cooling to 20° C. The crystalline product (mixture of three different products) was filtered off, washed with several portions of MeOH/water on the filter and dried at 50° C.

The 40/60 molar ratio of the two aldehydes statistically should lead to a molar ratio 36/48/16 in the product mixture, as shown in scheme V. The analysis of the product mixture with gas chromatography-mass spectroscopy (GC-MS) showed a ratio of 38/47/15. This ratio has been proven reproducible within a 2% range.

Preparation of SSMIX-07

SSMIX-07 has been prepared according to Scheme VI.

Scheme VI

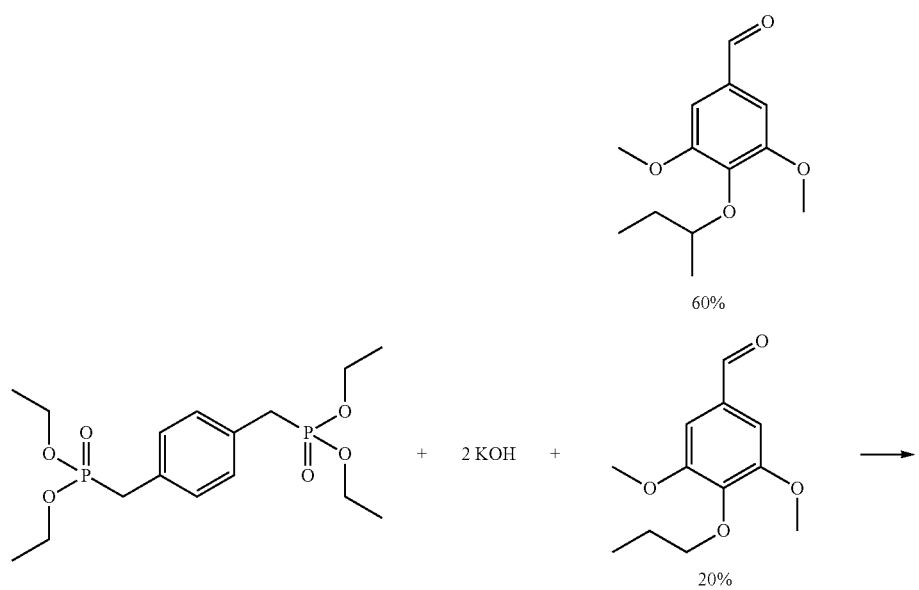

60%

+ 2 KOH +

20%

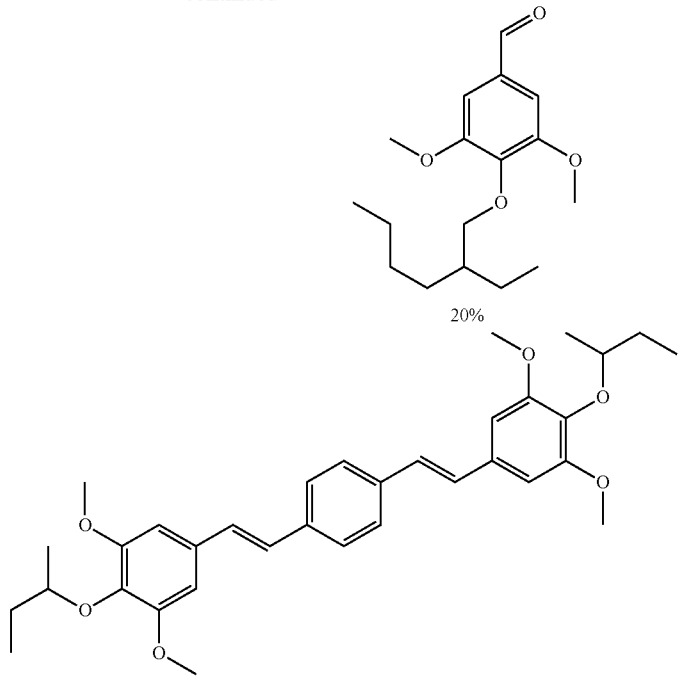
20%
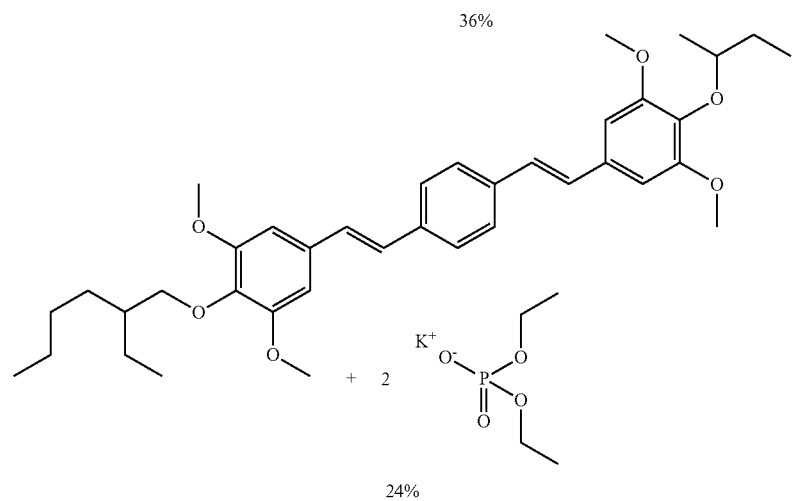
36%
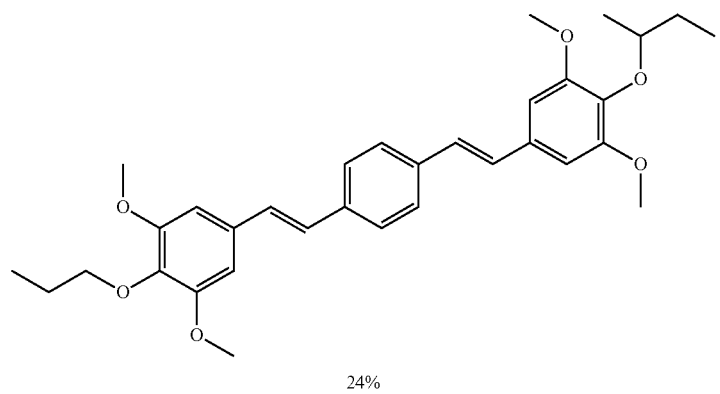
24%
24%

-continued

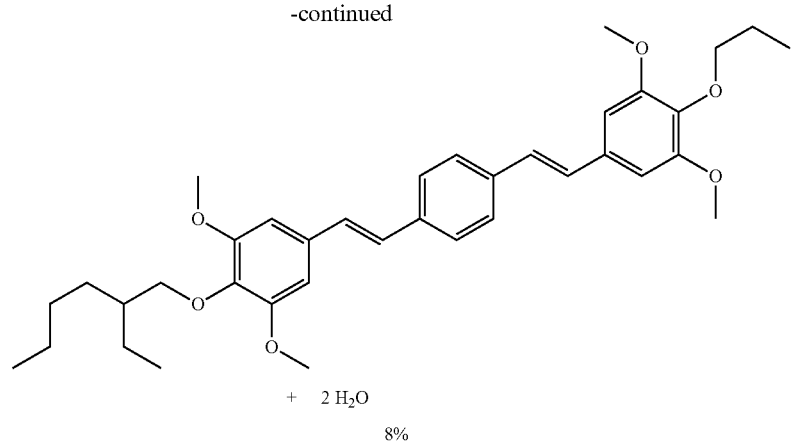

+ 2 H₂O

8%

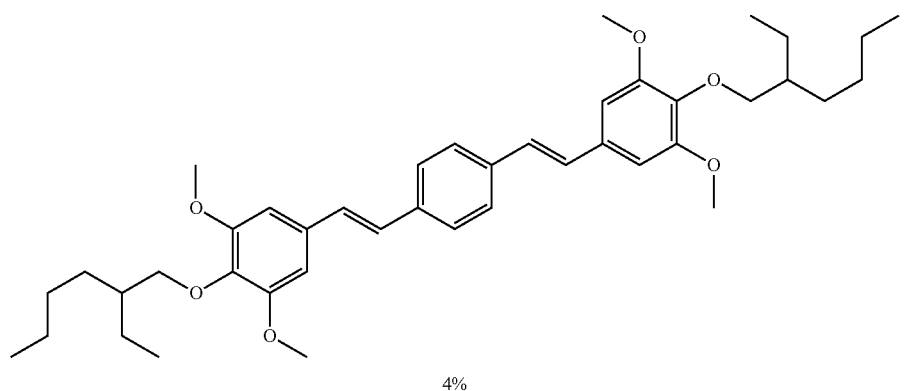

4%

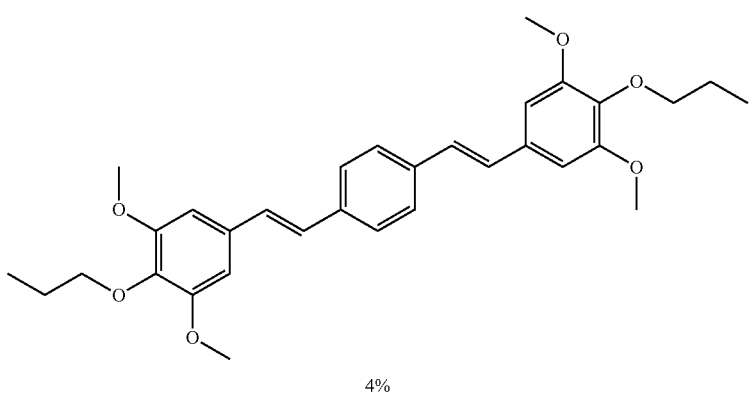

4%

To a mixture of 456 g (1.2 mol) p-xylene-bis-phosphonate, 156 g (504 mmol) of the crude intermediate 2-ethyl-hexyl alkylated syringaldehyde, 119 g (504 mmol) of the crude intermediate n-propyl alkylated syringaldehyde and 379 g (1512 mmol) of the crude intermediate 1-methyl-propyl alkylated syringaldehyde in 800 g THF, 230 g (3.5 mol) of KOH was added at room temperature. After heating the stirred reaction mixture at reflux for 3.5 hours, the reaction product was crystallised by adding a mixture of 1.19 kg methanol and 0.47 kg water, followed by further cooling to 20° C. The crystalline product (mixture of six products) was filtered off, washed with several portions of methanol/water on the filter and dried at 50° C. The yield was 550 g (theoretical yield of 84%) of the mixture of the six expected products in the expected ratio.

Preparation of SSMIX-08

SSMIX-08 has been prepared according to Scheme VII.

Scheme VII
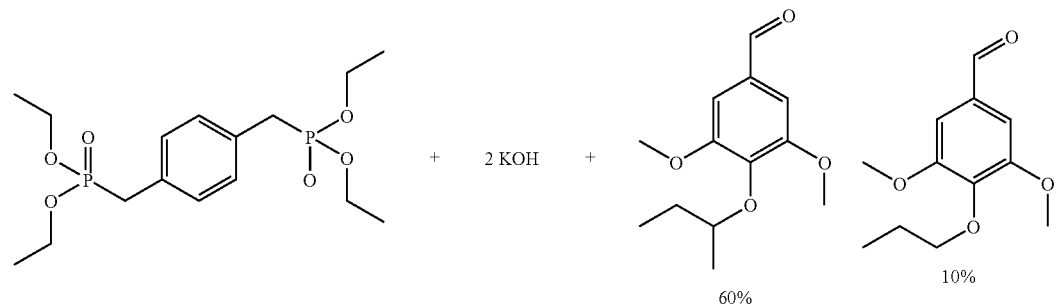
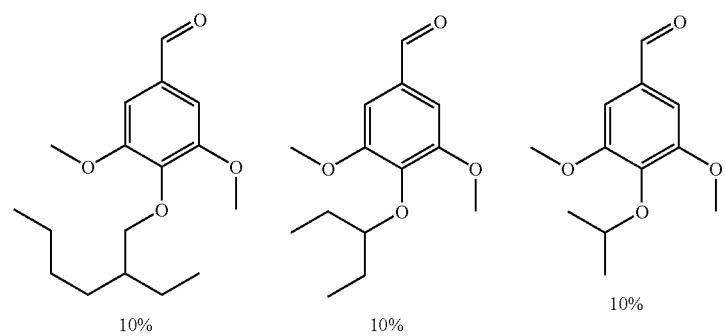
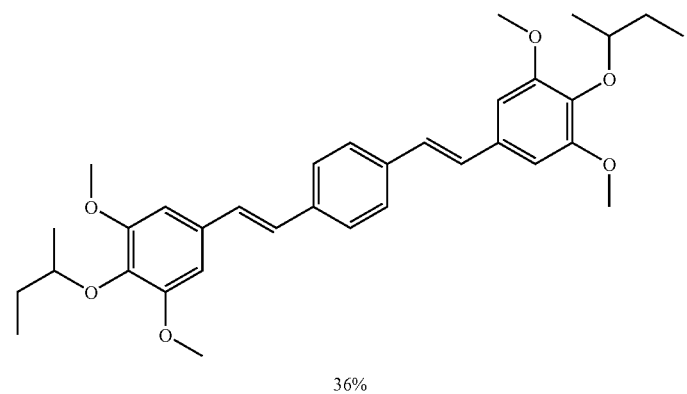 [SMILES: COc1cc(/C=C/c2ccc(/C=C/c3cc(OC)c(OC(C)C)c(OC)c3)cc2)cc(OC)c1OC(C)C]
36%
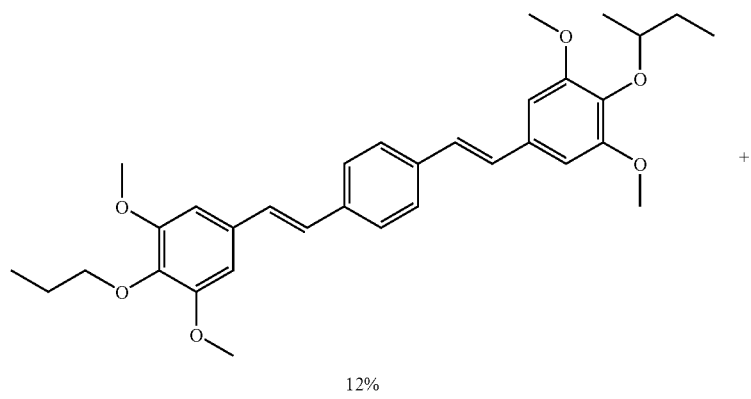
12%

-continued
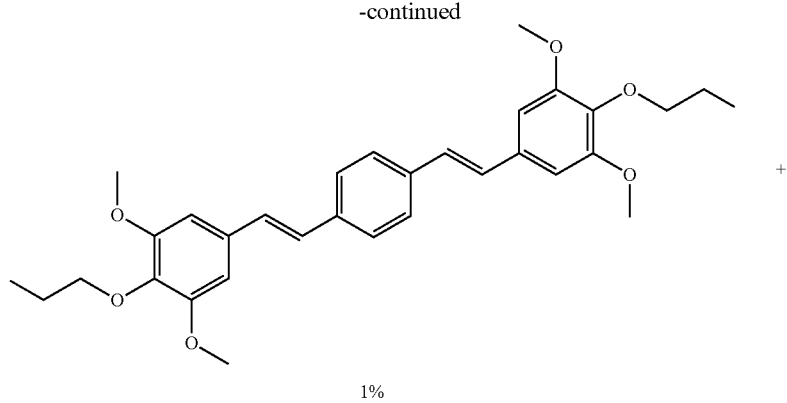
1%
+
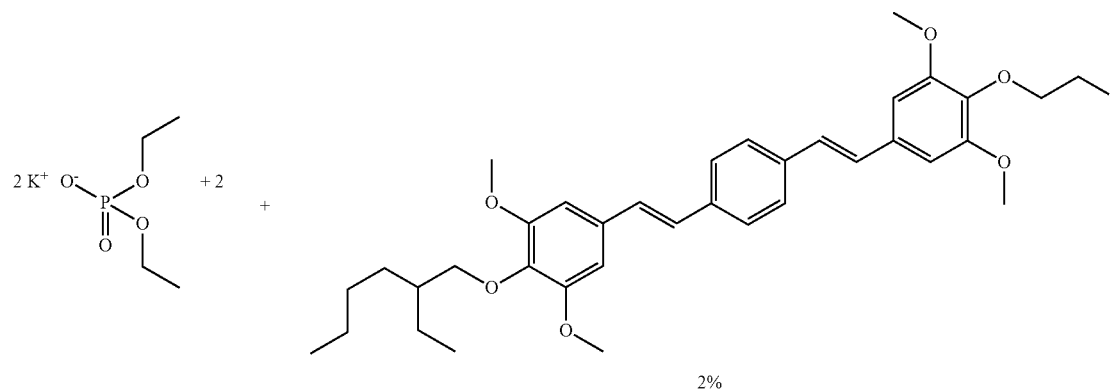
2K⁺ O⁻ + 2   +
2%
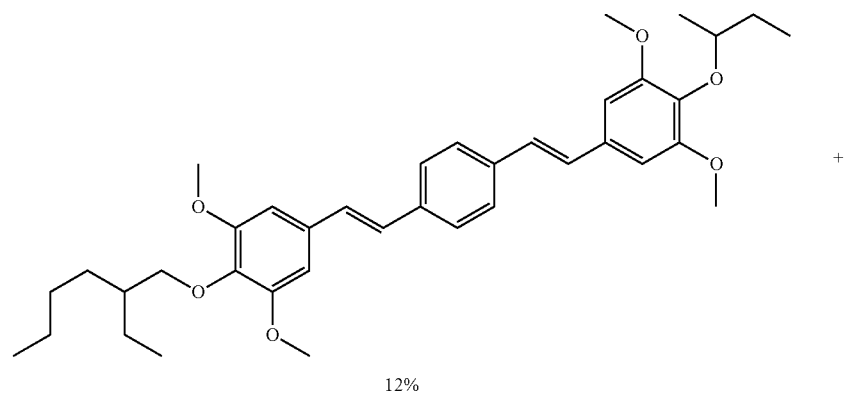
12%
+
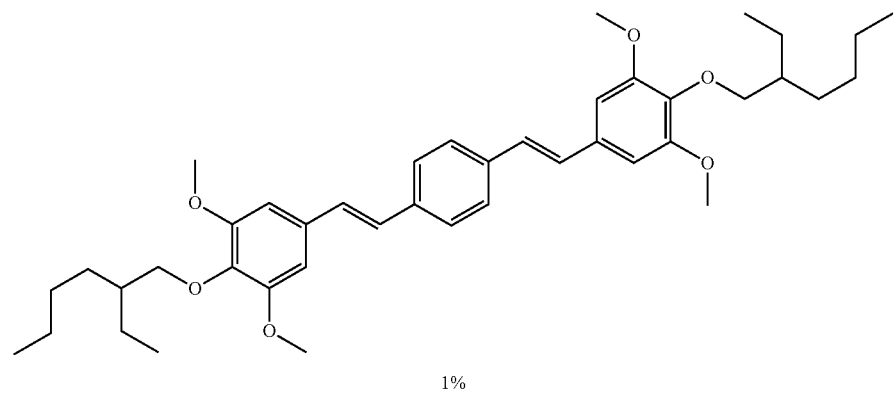
1%

-continued
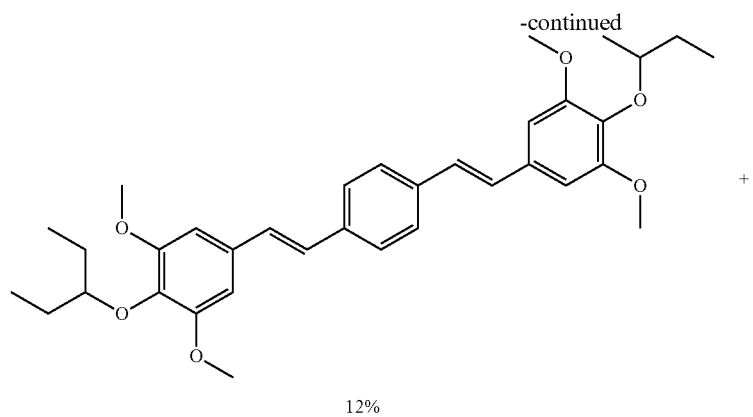
12%
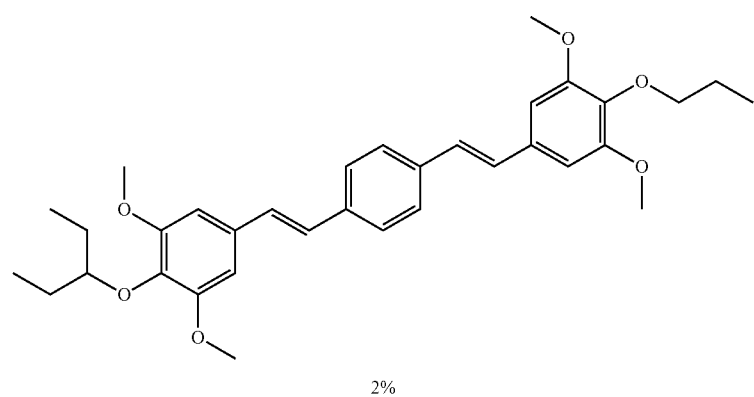
2%
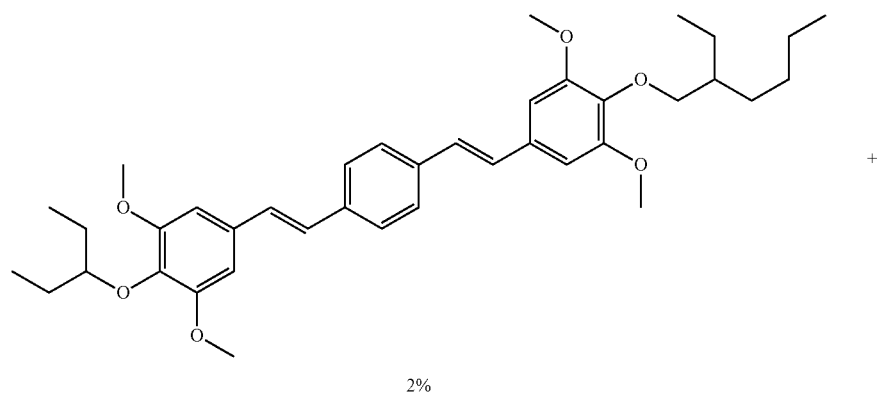
2%
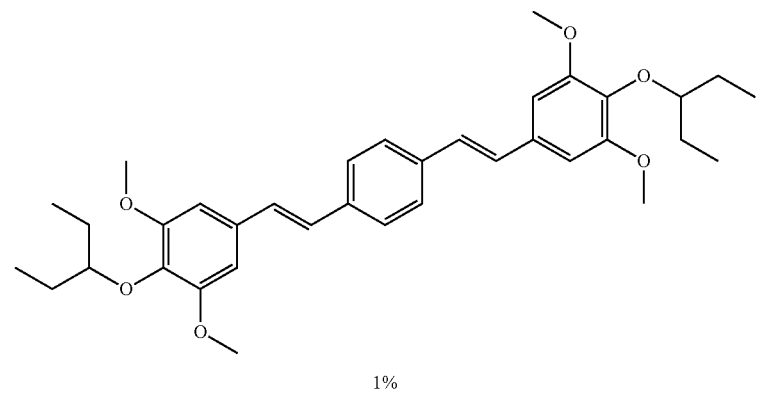
1%

-continued
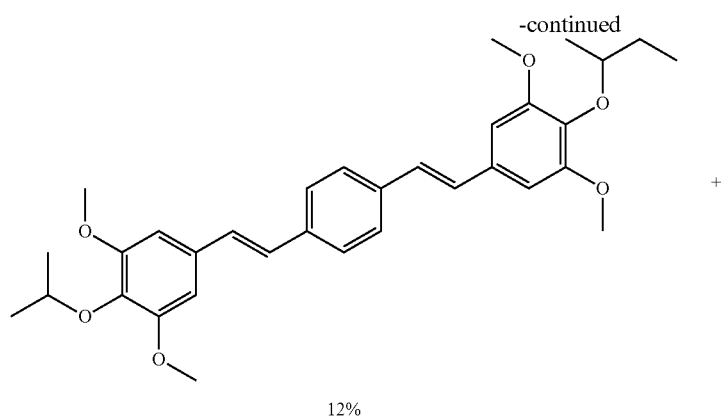
12%
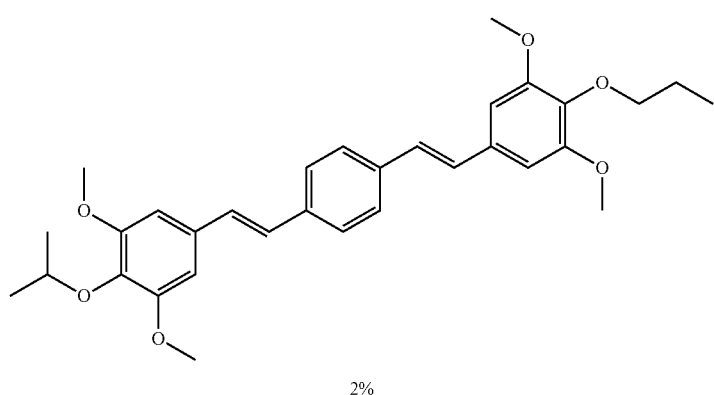
2%
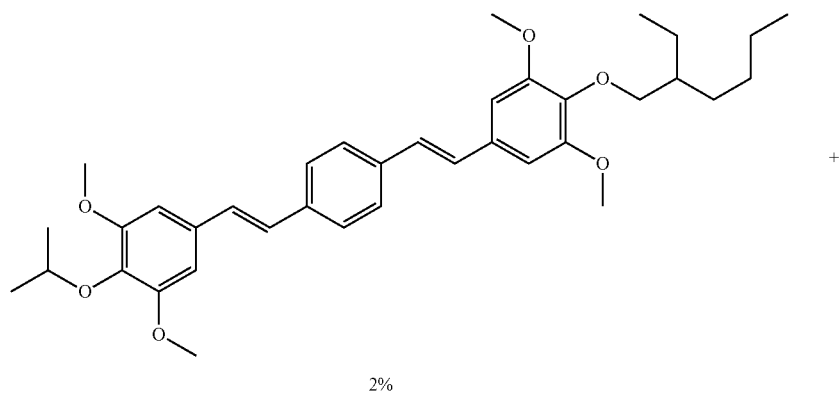
2%
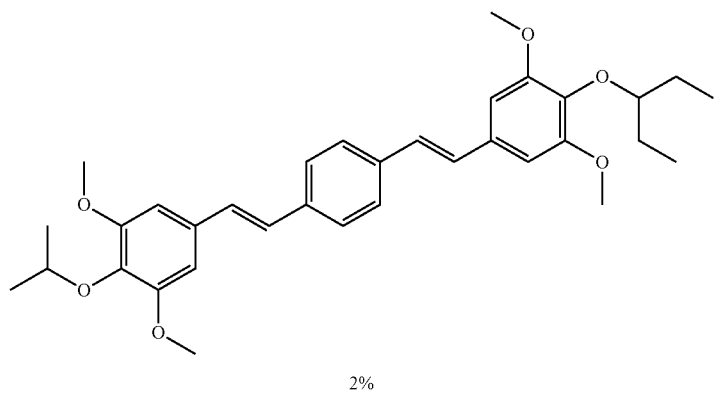
2%

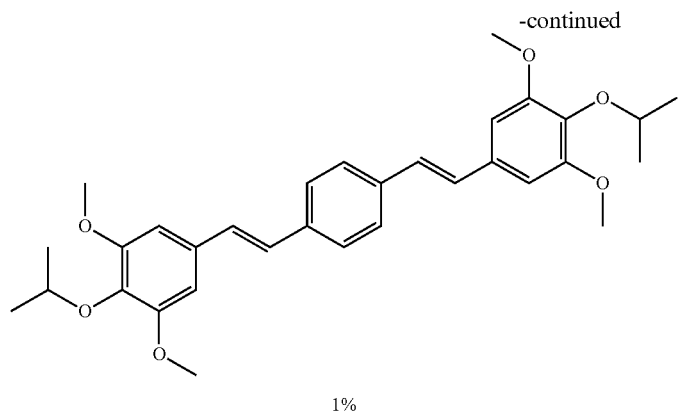

1%

To a mixture of 454 g (1.2 mol) p-xylene-bis-phosphonate, 65.2 g (230 mmol) of the crude intermediate i-propyl alkylated syringaldehyde, 70.4 g (230 mmol) of the crude intermediate 1-ethyl-propyl alkylated syringaldehyde, 85.6 g (230 mmol) of the crude intermediate 2-ethyl-hexyl alkylated syringaldehyde, 67.1 g (230 mmol) of the crude intermediate n-propyl alkylated syringaldehyde and 415 g (1380 mmol) of the crude intermediate 1-methyl-propyl alkylated syringaldehyde in 800 g THF, 230 g (3.5 mol) of KOH was added at room temperature. After heating the stirred reaction mixture at reflux for 3.5 hours, the reaction product was crystallised by adding a mixture of 1.19 kg methanol and 0.47 kg water, followed by further cooling to 20° C. The crystalline product (mixture of six products) was filtered off, washed with several portions of methanol/water on the filter and dried at 50° C. The yield is 510 g (theoretical yield of 78%) of the mixture of the fifteen expected products in the expected ratio.

Example 5

Preparation Printing Plate Precursors PPP-01 to PPP-13

Support

A 0.3 mm thick aluminum foil was degreased by spraying with an aqueous solution containing 26 g/l NaOH at 65° C. for 2 seconds and rinsed with demineralised water for 1.5 seconds. The foil was then electrochemically grained during 10 seconds using an alternating current in an aqueous solution containing 15 g/l HCl, 15 g/l $SO4^2$ ions and 5 g/l $Al^{3+}$ ions at a temperature of 37° C. and a current density of about 100 $A/dm^2$. Afterwards, the aluminum foil was desmutted by etching with an aqueous solution containing 5.5 g/l NaOH at 36° C. for 2 seconds and rinsed with demineralised water for 2 seconds. The foil was subsequently subjected to anodic oxidation during 15 seconds in an aqueous solution containing 145 g/l of sulfuric acid at a temperature of 50° C. and a current density of 17 $A/dm^2$, then washed with demineralised water for 11 seconds and post-treated for 3 seconds (by spray) with a solution containing 2.2 g/l PVPA at 70° C., rinsed with demineralised water for 1 seconds and dried at 120° C. for 5 seconds.

The support thus obtained was characterised by a surface roughness Ra of 0.35-0.4 μm (measured with interferometer NT1100) and had an anodic weight of 3.0 $g/m^2$.

Photopolymerizable Layers PL-01 to PL-13

The photopolymerizable layers PL-01 to PL-13 were prepared by coating the solutions of which the compositions are shown in Table 4, on the above described support. The wet coating thickness was 20 μm. After drying, a dry coating weight of 1.5 $g/m^2$ was obtained.

TABLE 4

| Ingredients | PL-01 (COMP) | PL-02 (COMP) | PL-03 (COMP) | PL-04 (COMP) | PL-05 (COMP) | PL-06 (COMP) | PL-07 (COMP) |
|---|---|---|---|---|---|---|---|
| Edaplan | 0.85 | 0.85 | 0.85 | 0.85 | 0.85 | 0.85 | 0.85 |
| MEK | 218.74 | 218.74 | 218.74 | 218.74 | 218.74 | 218.74 | 218.74 |
| SS-01 | 3.66 | — | — | — | — | — | — |
| SS-02 | — | 3.66 | — | — | — | — | — |
| SS-03 | — | — | 3.66 | — | — | — | — |
| SS-04 | — | — | — | 3.66 | — | — | — |
| SS-05 | — | — | — | — | 3.66 | — | — |
| SSMIX-01 | — | — | — | — | — | 3.66 | — |
| SSMIX-02 | — | — | — | — | — | — | 3.66 |
| Dowanol PM | 505.49 | 505.49 | 505.49 | 505.49 | 505.49 | 505.49 | 505.49 |
| FST426R | 11.83 | 11.83 | 11.83 | 11.83 | 11.83 | 11.83 | 11.83 |
| Mono Z1620 | 126.24 | 126.24 | 126.24 | 126.24 | 126.24 | 126.24 | 126.24 |
| Heliogene blue | 67.46 | 67.46 | 67.46 | 67.46 | 67.46 | 67.46 | 67.46 |
| Hostanox 03 | 0.43 | 0.43 | 0.43 | 0.43 | 0.43 | 0.43 | 0.43 |
| HABI | 5.53 | 5.53 | 5.53 | 5.53 | 5.53 | 5.53 | 5.53 |
| MBT | 0.26 | 0.26 | 0.26 | 0.26 | 0.26 | 0.26 | 0.26 |
| KL7177 | 59.53 | 59.53 | 59.53 | 59.53 | 59.53 | 59.53 | 59.53 |

TABLE 4-continued

| Ingredients | PL-08 (COMP) | PL-09 (COMP) | PL-10 (INV) | PL-11 (INV) | PL-12 (INV) | PL-13 (INV) |
|---|---|---|---|---|---|---|
| Edaplan | 0.85 | 0.85 | 0.85 | 0.85 | 0.85 | 0.85 |
| MEK | 218.74 | 218.74 | 218.74 | 218.74 | 218.74 | 218.74 |
| SSMIX-03 | 3.66 | — | — | — | — | — |
| SSMIX-04 | — | 3.66 | — | — | — | — |
| SSMIX-05 | — | — | 3.66 | — | — | — |
| SSMIX-06 | — | — | — | 3.66 | — | — |
| SSMIX-07 | — | — | — | — | 3.66 | — |
| SSMIX-08 | — | — | — | — | — | 3.66 |
| Dowanol PM | 505.49 | 505.49 | 505.49 | 505.49 | 505.49 | 505.49 |
| FST426R | 11.83 | 11.83 | 11.83 | 11.83 | 11.83 | 11.83 |
| Mono Z1620 | 126.24 | 126.24 | 126.24 | 126.24 | 126.24 | 126.24 |
| Heliogene blue | 67.46 | 67.46 | 67.46 | 67.46 | 67.46 | 67.46 |
| Hostanox 03 | 0.43 | 0.43 | 0.43 | 0.43 | 0.43 | 0.43 |
| HABI | 5.53 | 5.53 | 5.53 | 5.53 | 5.53 | 5.53 |
| MBT | 0.26 | 0.26 | 0.26 | 0.26 | 0.26 | 0.26 |
| KL7177 | 59.53 | 59.53 | 59.53 | 59.53 | 59.53 | 59.53 |

Preparation of the Overcoat Layer OC-01

The overcoat layer OC-01, also referred to as top layer, was applied from an aqueous solution. The composition of a 1000 g coating solution is defined in Table 5. The wet coating thickness was 45 µm. After drying at 110° C. for 2 minutes a dry coverage weight of 1.75 g/m² was obtained.

TABLE 5

| Ingredients OC-01 | g |
|---|---|
| PVA-1 | 17.04 |
| PVA-2 | 14.87 |
| PVA-3 | 7.43 |
| Acticide LA 1206 | 0.08 |
| Lupasol P | 0.40 |
| Lutensol A8 | 0.42 |
| Water | 960.00 |

Preparation of the Printing Plate Precursors PPP-01 to PPP-13

On top of the coated photopolymerizable layers PL-01 to PL-13, the above described overcoat layer OC-01 was applied. However, to better evaluate the propensity of the different photopolymerizable layers towards crystallization of the sensitizer, before application of the overcoat layer, the photopolymerizable layers were 'doped' with the sensitizers or mixture of sensitizers used in the photo-polymerizable layers. Thereto, after drying the photopolymerizable layers, the plates were fixed onto a flat surface, said surface kept at 50° C. A rubber roller was contaminated over its width with a small amount of sensitizer or sensitizer mixture. The contaminated rubber roller was then rolled over the photopolymerizable layer. The superfluous powder was removed by wiping it off with a cotton pad. After this 'doping' treatment, the overcoat layer was applied onto the 'doped' photopolymerizable layer, resulting in the printing plate precursors PPP-01 to PPP-13.

Evaluation of the Printing Plate Precursors PPP-01 to PPP-13

Each printing plate precursor was cut in two parts. One part was aged at 50° C. for 4 days, this part referred to as the 'aged' printing plate precursor. The other part is referred to as the 'fresh' part. The 'aged' and the 'fresh' parts were taped together again before exposure, pre-heat and development.

Exposure

Exposure was carried out at 1200 dpi on an Advantage DL3850 violet plate-setter, available from Agfa Graphics NV. The 'fresh' and 'aged' printing plate precursors were exposed through a UGRA step wedge (wedge constant=0.15). The exposure level chosen amounted to a solid step 1 (or even less) on the reproduction of the UGRA step wedge on the printing plate after exposure, pre-heat and development, which means that the printing plate precursor is largely underexposed. This exposure level allowed a better evaluation of the crystallization tendency of the precursors.

Another 'fresh' sample of each printing plate precursor was exposed in order to determine its sensitivity. This is the energy density (µJ/cm²) required to obtain a density of at least 97% of Dmax (Dmax is the maximum solid density that can be obtained) after pre-heat and processing on step 3 of the reproduction of the UGRA step wedge on the printing plate.

Pre-Heat

After exposure a pre-heat treatment was performed in the pre-heat unit of a VSP-85 processor (speed=1.2 m/min; temperature measured on the backside of the printing plate precursor=110° C.). A VSP-85 processor is commercially available from Agfa Graphics NV.

Development

After pre-heat, the plates were developed in a VSP-85 processor with PL10 developer, available from Agfa Graphics NV, at 24° C. and a speed of 1.2 m/min.

Printing

Printing was done on a Heidelberg GTO52 printing press equipped with a Dahlgren dampening system with K+E 800 ink and 100% Rotaprint Rotamatic as dampening solution.

Evaluation of Crystallization

The evaluation of the crystallization behaviour was performed on the 'aged' printing plates, after (under) exposure, pre-heat and development. Since the occurrence of microcrystals in the photo-polymerizable layer locally resulted in a decrease of the polymerization degree, a part of, or even the complete photo-polymerizable layer was removed after development, resulting in streaks of lower density. The occurrence of these impressions or streaks was visually evaluated and ranked, taking into account the number of impressions or streaks, their wideness and their deepness. When the complete layer was removed, the lowest density (Dmin) was observed. The samples were ranked according to the following scale:

6: No impressions visible
5: Small impressions visible with no Dmin areas
4: Small impressions visible with almost no Dmin areas
3: Impressions visible with limited Dmin areas 2: Impressions visible with Dmin areas over the complete width of the impressions 1: Impressions visible with large and wide Dmin areas The results of the evaluation of the crystallization tendency of the printing plates PP-01 to PP-13 are shown in Table 6, together with some lithographic properties.

TABLE 6

| PPP | Sensitivity 'fresh' plate ($\mu J/m^2$) | Level of impressions or streaks 'aged' plate | Dot Gain Plate @ 40% @ 110 lpi of 'fresh' plate | Lithographic performance 'fresh' plate |
|---|---|---|---|---|
| PPP-1 (COMP) | 33 | 1 | 10.6 | OK |
| PPP-2 (COMP) | 36 | 1 | 10.5 | OK |
| PPP-3 (COMP) | 32 | 1 | 11.0 | OK |
| PPP-4 (COMP) | 31 | 1 | 9.8 | OK |
| PPP-5 (COMP) | 30 | 1 | 9.8 | OK |
| PPP-6 (COMP) | 32 | 2 | 9.7 | OK |
| PPP-7 (COMP) | 30 | 1 | 11.5 | OK |
| PPP-8 (COMP) | 34 | 3 | 10.8 | OK |
| PPP-9 (COMP) | 32 | 1 | 9.9 | OK |
| PPP-10 (INV) | 32 | 6 | 9.9 | OK |
| PPP-11 (INV) | 31 | 6 | 10.1 | OK |
| PPP-12 (INV) | 33 | 6 | 10.4 | OK |
| PPP-13 (INV) | 31 | 6 | 10.2 | OK |

The invention claimed is:

1. A lithographic printing plate precursor comprising an image-recording layer, said image-recording layer being photo-polymerizable upon exposure with light having a wavelength of from 300 to 500 nm and comprising a mixture of sensitizers, said mixture comprises at least three different sensitizers according to Formula I,

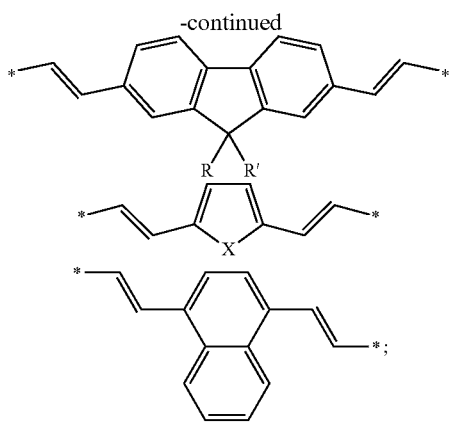

Formula I wherein $R^1$ to $R^6$ independently represent a hydrogen atom, an optionally substituted alkyl group, an optionally substituted alkoxy group, a cyano group, a halogen atom, a dialkylamino group, an alkylarylamino group or a diarylamino group;

L is a divalent linking group selected from the group consisting of:

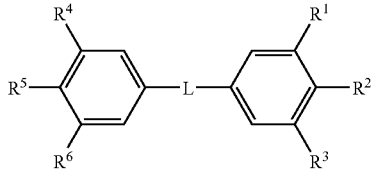

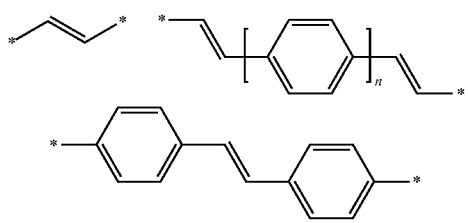

-continued

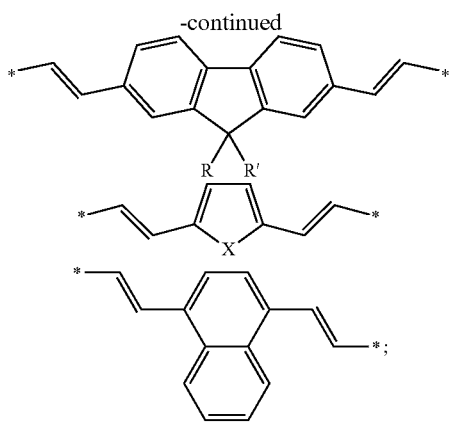

n is an integer from 0 to 2;

X represents S, O or $NR^x$;

* represents the linking positions of the linking group L to the phenyl groups of Formula I;

R, R' and $R^x$ represent an optionally substituted alkyl group;

wherein for at least two sensitizers of said mixture at least one of $R^1$ to $R^6$ contains an asymmetric C-atom and the total amount of two or more sensitizers of which at least one of $R^1$ to $R^6$ contains an asymmetric C-atom is more than 65 percent by weight relative to the total weight of said mixture.

2. The lithographic printing plate precursor according to claim 1, wherein $R^1$ to $R^6$ are alkoxy groups.

3. The lithographic printing plate precursor according to claim 2, wherein $R^1$, $R^3$, $R^4$ and $R^6$ are methoxy groups and $R^5$ and $R^2$ are alkoxy groups having 3 to 15 C-atoms.

4. A method of making a printing plate comprising the steps of:

providing a lithographic printing plate precursor as described in claim 3;

image-wise exposing said precursor with a laser having a wavelength from 300 to 500 nm;

optionally pre-heating said exposed precursor; and developing said precursor.

5. The method according to claim 4, wherein said light has an energy density, measured on the surface of the plate, of 100 $\mu J/cm^2$ or less.

6. The method according to claim 4, wherein the development is performed in a gum-solution.

7. The lithographic printing plate according to claim 1, wherein said mixture of sensitizers comprises a mixture of sensitizers according to formula II,

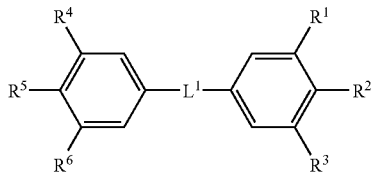

Formula II wherein $R^1$ to $R^6$ independently represent a hydrogen atom, an optionally substituted alkyl group, an optionally substituted alkoxy group, a cyano group, a halogen atom, a dialkylamino group, an alkylarylamino group or a diarylamino group;

$L^1$ is a divalent linking group selected from the list consisting of:

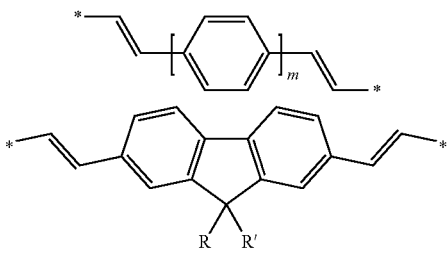

wherein m is 1 or 2; and represents the linking positions of the linking group $L^1$ to the phenyl groups of Formula II;

R and R' represent an optionally substituted alkyl group.

8. The lithographic printing plate precursor according claim 1, wherein the photopolymerizable coating further comprises a hexaarylbisimidazole compound as initiator.

9. The lithographic printing plate precursor according to claim 8, wherein the photopolymerizable layer further comprises a mercaptobenzthiazole compound as co-initiator.

10. A method of making a printing plate comprising the steps of:
providing a lithographic printing plate precursor as described in claim 1;
image-wise exposing said precursor with a laser having a wavelength from 300 to 500 nm;
optionally pre-heating said exposed precursor; and
developing said precursor.

11. The method according to claim 10, wherein said light has an energy density, measured on the surface of the plate, of 100 μJ/cm² or less.

12. The method according to claim 10, wherein the development is performed in a gum-solution.

13. A method of making a printing plate comprising the steps of:
providing a lithographic printing plate precursor as described in claim 2;
image-wise exposing said precursor with a laser having a wavelength from 300 to 500 nm;
optionally pre-heating said exposed precursor; and
developing said precursor.

14. The method according to claim 13, wherein the development is performed in a gum-solution.

15. The method according to claim 13, wherein said light has an energy density, measured on the surface of the plate, of 100 μJ/cm² or less.

* * * * *